United States Patent
Deshmukh et al.

(10) Patent No.: US 9,682,068 B2
(45) Date of Patent: Jun. 20, 2017

(54) TRANSDERMAL THERAPEUTIC SYSTEM FOR EXTENDED DOSING OF PRAMIPEXOLE IN TREATING NEUROLOGICAL DISORDERS

(71) Applicant: MYLAN INC., Morgantown, WV (US)

(72) Inventors: Abhijit Mukund Deshmukh, Secundarabad (IN); Akhilesh Dixit, Nagpur (IN); Prasanna Kumar, Hyderabad (IN); Vikram Bindra, Panipat (IN)

(73) Assignee: Mylan Inc., Canonsburg, PA (US)

( * ) Notice: Subject to any disclaimer, the term of this patent is extended or adjusted under 35 U.S.C. 154(b) by 0 days.

(21) Appl. No.: 14/893,020

(22) PCT Filed: May 19, 2014

(86) PCT No.: PCT/IB2014/061545
§ 371 (c)(1),
(2) Date: Nov. 20, 2015

(87) PCT Pub. No.: WO2014/188329
PCT Pub. Date: Nov. 27, 2014

(65) Prior Publication Data
US 2016/0113908 A1    Apr. 28, 2016

(30) Foreign Application Priority Data
May 20, 2013 (IN) .......................... 1787/MUM/2013

(51) Int. Cl.
*A61K 31/428* (2006.01)
*A61K 47/32* (2006.01)
(Continued)

(52) U.S. Cl.
CPC .......... *A61K 31/428* (2013.01); *A61F 13/025* (2013.01); *A61F 13/0259* (2013.01); *A61F 13/0283* (2013.01); *A61K 9/7061* (2013.01); *A61K 9/7069* (2013.01); *A61F 2013/0296* (2013.01)

(58) Field of Classification Search
CPC ................ A61F 13/025; A61F 13/0259; A61F 13/0283; A61F 2013/0293; A61F 31/428; A61F 47/32; A61F 9/7053; A61F 9/7061; A61F 9/7069; A61F 9/7084
See application file for complete search history.

(56) References Cited

U.S. PATENT DOCUMENTS 3,598,122 A    8/1971    Zaffaroni
3,598,123 A    8/1971    Zaffaroni
(Continued)

FOREIGN PATENT DOCUMENTS

IN    WO 2012140604    * 10/2012    .............. A61K 9/20

*Primary Examiner* — Ernst V Arnold

(57) ABSTRACT

This disclosure relates to a transdermal therapeutic system (TTS) containing pramipexole or related compounds and methods of making the system as well as its use in administering such compounds as a single dose over an extended period, for example, one week. The system comprises an acrylic-based or silicone-based matrix layer containing pramipexole at concentrations of at least about 5 wt. % of the matrix, which is resistant to crystallizing and discoloration of the active ingredient even when stored over long periods.

25 Claims, 9 Drawing Sheets

(51) Int. Cl.
   *A61K 9/70*   (2006.01)
   *A61F 13/02*  (2006.01)

(56) References Cited

U.S. PATENT DOCUMENTS

| | | |
|---|---|---|
| 3,731,683 A | 5/1973 | Zaffaroni |
| 3,797,494 A | 3/1974 | Zaffaroni |
| 4,031,894 A | 6/1977 | Urquhart et al. |
| 4,201,211 A | 5/1980 | Chandrasekaran et al. |
| 4,286,592 A | 9/1981 | Chandrasekaran et al. |
| 4,314,557 A | 2/1982 | Chandrasekaran et al. |
| 4,379,454 A | 4/1983 | Campbell et al. |
| 4,435,180 A | 3/1984 | Leeper |
| 4,559,222 A | 12/1985 | Enscore et al. |
| 4,568,343 A | 2/1986 | Leeper et al. |
| 4,588,580 A | 5/1986 | Gale et al. |
| 4,645,502 A | 2/1987 | Gale et al. |
| 4,698,062 A | 10/1987 | Gale et al. |
| 4,704,282 A | 11/1987 | Campbell et al. |
| 4,725,272 A | 2/1988 | Gale |
| 4,781,924 A | 11/1988 | Lee et al. |
| 4,788,062 A | 11/1988 | Gale et al. |
| 4,816,258 A | 3/1989 | Nedberge et al. |
| 4,849,226 A | 7/1989 | Gale |
| 4,904,475 A | 2/1990 | Gale et al. |
| 4,908,027 A | 3/1990 | Enscore et al. |
| 4,917,895 A | 4/1990 | Lee et al. |
| 4,938,759 A | 7/1990 | Enscore et al. |
| 4,943,435 A | 7/1990 | Baker et al. |
| 5,004,610 A | 4/1991 | Osborne et al. |
| 5,071,656 A | 12/1991 | Lee et al. |
| 5,141,750 A | 8/1992 | Lee et al. |
| 5,342,623 A | 8/1994 | Enscore et al. |
| 5,411,740 A | 5/1995 | Lee et al. |
| 5,635,203 A | 6/1997 | Gale et al. |
| 7,344,733 B2 | 3/2008 | Beier et al. |
| 2006/0182791 A1* | 8/2006 | Theobald ............ A61K 31/428 424/449 |
| 2008/0076913 A1 | 3/2008 | Dellinger et al. |
| 2011/0151003 A1 | 6/2011 | Jackson et al. |

* cited by examiner

| Exp No | Composition details |
|---|---|
| 087 | Batch composition using drug dispersed in Bio PSA |
| 089 | Batch composition using drug dispersed in PIB |
| 092 & 095 | Batch compositions using DT 2287 A |

TRANSDERMAL THERAPEUTIC SYSTEM FOR EXTENDED DOSING OF PRAMIPEXOLE IN TREATING NEUROLOGICAL DISORDERS

FIELD

This disclosure relates generally to transdermal drug delivery, and more particularly to a transdermal therapeutic system (TTS) containing pramipexole or related compounds and methods of administering such an active agent over extended periods. The invention additionally relates to a transdermal composition containing pramipexole at concentrations of at least about 5 wt. %, which is resistant to crystallizing and discoloration of the active ingredient even when stored over long periods.

BACKGROUND

The disclosure relates generally to transdermal drug delivery, and more particularly to transdermal compositions and methods of administering an active agent comprising pramipexole and/or its related compounds in a single dose for extended periods, typically two days or greater. The invention additionally relates to a non-occlusive transdermal therapeutic system semi-solid composition containing pramipexole, which is chemically stable.

The transdermal route of parenteral drug delivery provides many advantages over other administrative routes. Transdermal drug delivery devices, including multilaminates and monoliths, for delivering a wide variety of drugs or other beneficial agents are described in U.S. Pat. Nos. 3,598,122; 3,598,123; 3,731,683; 3,797,494; 4,031,894; 4,201,211; 4,286,592; 4,314,557; 4,379,454; 4,435,180; 4,559,222; 4,568,343; 4,588,580; 4,645,502; 4,698,062; 4,704,282; 4,725,272; 4,781,924; 4,788,062; 4,816,258; 4,849,226; 4,904,475; 4,908,027; 4,917,895; 4,938,759; 4,943,435; 5,004,610; 5,071,656; 5,141,750; 5,342,623; 5,411,740; and 5,635,203.

One problem associated with the devices of the prior art is degradation of the pharmaceutical active ingredient, as well as certain contents of the device, such as permeation enhancers, matrix materials, or other components. Degradation can result from both internal and external conditions. Internal conditions include the presence of inactive ingredients such as acid, base and oxidants, which may react with and degrade the active pharmaceutical ingredients (APIs). Impurities from these inactive ingredients not only undesirably break down these materials, but can also cause discoloration and formation of odors even within a system which separates the active ingredients from external conditions, such as heat, light, moisture and oxygen, e.g., by use of an envelope or pouch. Devices susceptible to degradation cannot be stored for a commercially reasonable amount of time, thus causing practical problems in their distribution.

Pramipexole is used for the treatment of neurological disclosures, e.g., Parkinson's disease. Pramipexole's structural formula is set out below.

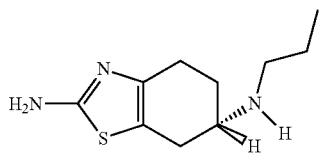

As a dopamine agonist, pramipexole [2-amino-6-n-propylamino-4,5,6,7-tetrahydrobenzo-thiazole] binds with high selectivity and specificity to the $D_2$ and $D_3$ receptors. Owing to its stimulating effect on the dopamine receptors in the corpus striatum, pramipexole produces a reduction in Parkinson's tremors. When administered orally, the daily dose is approximately from 1.5 to 4.5 mg with a bioavailability of 90%. However, the administration of even small amounts of pramipexole is associated with considerable side-effects in the patient.

A transdermal therapeutic system avoids side-effects that occur in the case of oral administration of pramipexole. Transdermal administration furthermore has the advantage that the active ingredient, after permeation through the skin, has a direct systemic action, as a result of which a constant blood plasma level can be guaranteed. Hepatic metabolism of the active ingredient is also circumvented. Gastrointestinal side-effects are avoided.

EP-B1-0 428 038 discloses a transdermal system having a content of pramipexole and a) an active-ingredient-impermeable backing layer which is at the same time constructed as a covering plaster, b) an active-ingredient-containing reservoir (preferred carrier for the active ingredient is an emulsion-polymerised polyacrylate of the type Eudragit NE 30 $D^R$ produced by Rohm GmbH, Darmstadt) and c) a peel-off protective film (release liner).

Owing to surfactants or plasticizers and surface-active substances used in an emulsion-polymerized polyacrylate, a TTS produced according to EP-B1-0 428 038 does not exhibit sufficient stability of the active ingredient. In that matrix, pramipexole decomposes very rapidly, with discoloration occurring. In addition, the active ingredient crystallizes out, resulting in insufficient storage stability.

U.S. Published Application 2008/076913 discloses a pharmaceutical composition for transdermal or transmucosal delivery of an active agent such as pramipexole to treat a movement disorder such as Parkinson's disease. The composition includes an alkanolamine as a permeation enhancer with a carrier of water and at least one short-chain alcohol and with the composition having a neutral pH. The composition provides controlled and sustained release of the active agent suitable for daily administration.

U.S. Published Application 2011/0151003 discloses a transdermal drug delivery device package which comprises a backing layer substantially impervious to the drug being delivered, a drug reservoir adhesive layer, a skin contact adhesive layer wherein each adhesive layer provides a different rate of drug delivery therefrom, and a release liner whose removal exposes the skin contact adhesive layer. The resulting dosage units are stored in appropriate packaging until used.

U.S. Pat. No. 7,344,733 describes preparation of a matrix-controlled transdermal therapeutic system for the use of pramipexole and ropirinole, which contains acrylic, silicone and polyisobutene (PIB) pressure-sensitive adhesives (PSAs). The '733 patent, teaches actives ranging from 2 to 15% by weight of the weight of the matrix, as well as exemplified embodiments which use a concentration of not more than 4% w/w active ingredient which is stable in terms of discoloration, with no crystal growth and a flux profile of only 24 hours.

U.S. patent application Ser. No. 13/624,390, filed Sep. 21, 2012 discloses transdermal delivery devices for drugs which are subject to degradation during storage by hydrolysis and/or oxidation, e.g., rivastigmine.

U.S. patent application Ser. No. 13/570,593, filed Aug. 9, 2012 discloses a method for treating severe headaches, e.g., cluster headaches and migraines, using transdermal administration of pramipexole.

It would be desirable to provide a transdermal drug delivery device package which provides controlled and sustained release of an active agent, e.g., dopamine agonist, such as pergolide, lisuride and/or pramipexole, for an extended period of time of more than one day, e.g., two days, three days, or a week or more, to treat hypokinetic disorders such as Parkinson's disease. It would further be desirable to provide a transdermal drug delivery device package which allows the use of highly concentrated active ingredient(s), e.g., pramipexole at greater than about 5 wt. % of the matrix in which it found, which exhibits a therapeutically effective flux profile over an extended period, e.g., at least two days, a one week period or even longer. It would also be desirable to provide a transdermal drug delivery device package which, while using highly concentrated active ingredient(s), still exhibits formulation stability of its active ingredient(s). Such a device would avoid or minimize substantial discoloration or substantial crystal growth over extended storage periods, e.g., at least one month or longer.

SUMMARY

In one aspect, the present disclosure relates to a transdermal therapeutic system (TTS) for the administration of one or more active ingredients selected from the group consisting of pramipexole, pharmaceutically acceptable pramipexole salts, and pharmaceutically acceptable pramipexole derivatives. The system comprises: (i) a substantially active-ingredient-impermeable backing layer, (ii) at least one matrix layer which contains at least about 5% w/w active ingredient(s), and (iii) a substantially impermeable protective release liner layer which releasably contacts the matrix layer or another adhesive layer; wherein 1) the matrix layer comprises an adhesive selected from acrylate-based adhesive and silicone-based adhesive, 2) the transdermal therapeutic system provides a therapeutically effective administration of the active ingredient(s), at a flux rate ranging from about 1 $\mu g/cm^2/hr$ to about 13 $\mu g/cm^2/hr$ for at least 48 hours after treatment is initiated, and 3) the matrix layer is color-stable and lacks crystal growth of the active ingredient, over an extended storage period of at least one of 30 or more days, 90 or more days, and 180 or more days.

In certain embodiments of this aspect of the disclosure, the active-ingredient-containing matrix layer contains from about 5% to about 10% w/w active ingredient(s) and contains less than about 1 wt. % pramipexole-related impurities after two months of storage at about 40° C.

In certain embodiments of this aspect of the disclosure, the active-ingredient-containing matrix layer contains from about 5% to about 10% w/w active ingredient(s) and contains less than about 0.5 wt. % pramipexole-related impurities after two months of storage at about 40° C.

In some embodiments of this aspect of the disclosure, the transdermal therapeutic system's active-ingredient-containing matrix layer contains from about 5% to about 10° A w/w active ingredient(s) and provides a therapeutically effective flux rate ranging from about 1 $\mu g/cm^2/hr$ to about 13 $\mu g/cm^2/hr$ between the $48^{th}$ hour and $168^{th}$ hour after treatment is initiated, e.g., the active-ingredient-containing matrix layer contains from about 5.5% to about 7% w/w active ingredient(s) and provides a therapeutically effective flux rate ranging from about 1 $\mu g/cm^2/hr$ to about 6 $\mu g/cm^2/hr$ between the $48^{th}$ hour and $168^{th}$ hour after treatment is initiated, e.g., the active-ingredient-containing matrix layer provides a therapeutically effective flux rate ranging from about 1.2 $\mu g/cm^2/hr$ to about 5.0 $\mu g/cm^2/hr$ between the $48^{th}$ hour and $168^{th}$ hour after treatment is initiated.

In certain embodiments of this aspect of the disclosure, the active ingredient comprises pramipexole free base.

In various embodiments of this aspect of the disclosure, the active ingredient comprises one or more salts pramipexole comprising reaction products of pramipexole or a pramipexole derivative and an acid.

In some embodiments of this aspect of the disclosure, the matrix layer is self-adhesive.

In certain embodiments of this aspect of the disclosure, the matrix layer comprises an acrylate-based adhesive comprising polyacrylate lacking a carboxylic acid functional group.

In some embodiments of this aspect of the disclosure, the matrix layer comprises a polymer material free of solubilizers and/or crystal growth inhibitors.

In various embodiments of this aspect of the disclosure, the matrix layer comprises 0 wt. % to about 20 wt. % of a solubilizer and/or crystal growth inhibitor, e.g., from about 2.5 wt. % to about 17.5 wt. % of a solubilizer and/or crystal growth inhibitor, say, wherein the matrix layer comprises about 10 wt. % of a solubilizer and/or crystal growth inhibitor.

In some embodiments of this aspect of the disclosure, the solubilizer and/or crystal growth inhibitor is selected from the group consisting of optionally saturated and/or unsaturated fatty alcohols each containing from 8 to 18 carbon atoms; tea tree oil; saturated and/or unsaturated cyclic ketones; alkyl methyl sulfoxides; saturated and/or unsaturated fatty acids each containing from 8 to 18 carbon atoms; esters and salts thereof; natural vitamin E (Copherol® F1300); synthetic vitamin E and/or vitamin E derivatives; sorbitan fatty acid esters and/or ethoxylated sorbitan fatty acid esters; azones (laurocapram); 1-alkylpyrrolidone; polyvinylpyrrolidone; block copolymers of polyethylene glycol and dimethylsiloxane with a cationic group at one end; polysiloxanes; polyoxyethylene-10-stearyl ether; mixture of polyoxyethylene-10-stearyl ether and glyceryl dilaurate; dodecyl-2-(N,N-dimethylamino)-propanol tetradecanoate and/or dodecyl-2-(N,N-dimethylamino)-propionate; N-acetylprolinate esters with >8 carbon atoms; non-ionic surfactants, for example lauryl ethers and/or esters of polyoxyethylene; dimethyl(arylimino)sulfuran; mixture of oleic acid analogues and propylene glycol; mixture of octyl salicylate, isopropyl myristate, isopropyl palmitate, octylmethoxy cinnamate and laurocapram or a mixture of individual components; phospholipids; highly dispersed silicon dioxide (Aerosil®); polyoxyethylene-7-glycerol monococoate (Cetiol® HE); 2-octyldodecanol (Eutanol® G) or a mixture of various individual components, e.g., wherein the solubilizer and/or crystal growth inhibitor is polyvinylpyrrolidone.

In another aspect, the disclosure relates to a method for preparing a transdermal therapeutic system which comprises: i) providing an active-ingredient containing matrix layer by: 1) forming a mixture comprising a) active ingredient pramipexole free base, b) a solvent selected from methanol, ethanol, n-propanol, iso-propanol, n-butanol, iso-butanol and tert-butanol, acetone, pentane, hexane, heptane, ethyl acetate, isopropanol, toluene, xylene, 2,4-pentanedione, and water, and c) an optional solubilizer and/or crystal growth inhibitor; 2) dissolving the mixture to provide a dissolved mixture; 3) combining the dissolved mixture with a matrix forming ingredient to form a pramipexole-containing matrix precursor mixture; and 4) optionally degassing the matrix precursor mixture to provide a degassed matrix precursor mixture; ii) coating one side of a release liner film with the matrix precursor mixture or optionally degassed matrix precursor mixture; and iii) laminating a backing film to the coated side of the release liner film.

In certain embodiments of this aspect of the present disclosure, the solvent comprises ethanol, the dissolving step comprises sonication, the optional solubilizer and/or crystal growth inhibitor comprises polyvinylpyrrolidone, and the matrix forming ingredient comprises an adhesive selected from acrylate-based adhesive and silicone-based adhesive.

In various embodiments of this aspect of the present disclosure, the adhesive comprises polyacrylate lacking a carboxylic acid functional group.

In some embodiments of this aspect of the present disclosure, the solubilizer and/or crystal growth inhibitor is polyvinylpyrrolidone.

In certain embodiments of this aspect of the present disclosure, the adhesive comprises silicone-based adhesive, silicone oil and colloidal silicon dioxide.

In yet another aspect, the disclosure relates to a method for preparing a transdermal therapeutic system which comprises: i) providing an active-ingredient containing matrix layer by: 1) forming a mixture comprising a) active ingredient pramipexole free base, b) a solvent and/or dispersant selected from methanol, ethanol, n-propanol, iso-propanol, n-butanol, iso-butanol and tert-butanol, acetone, pentane, hexane, heptane, ethyl acetate, isopropanol, toluene, xylene, 2,4-pentanedione, and water, and c) an optional solubilizer and/or crystal growth inhibitor; 2) dissolving and/or dispersing the mixture to provide a dissolved and/or dispersed mixture; 3) combining the dissolved and/or dispersed mixture with a matrix forming ingredient to form a pramipexole-containing matrix precursor mixture; and 4) optionally degassing the matrix precursor mixture to provide a degassed matrix precursor mixture; ii) coating one side of a release liner film with the matrix precursor mixture or optionally degassed matrix precursor mixture; and iii) laminating a backing film to the coated side of the release liner film.

In still another aspect, the present disclosure relates to a method for administering pramipexole to a human subject in need thereof, which method comprises: i) providing a transdermal dosage form comprising a therapeutically effective amount of active ingredient pramipexole or a pharmaceutically acceptable salt thereof in at least one matrix layer which contains at least about 5% w/w active ingredient(s), and further wherein 1) the matrix layer comprises an adhesive selected from acrylate-based adhesive and silicone-based adhesive, 2) the transdermal therapeutic system provides a therapeutically effective administration of the active ingredient(s), at a flux rate ranging from about 1 µg/cm²/hr to about 13 µg/cm²/hr for at least 48 hours after treatment is initiated, and 3) the matrix layer is color-stable and lacks crystal growth of the active ingredient, over an extended storage period of at least one of 30 or more days, 90 or more days, and 180 or more days; and ii) applying the dosage form onto an area of skin of the subject in an amount sufficient to provide a therapeutic concentration of pramipexole in the bloodstream of the subject.

In some embodiments of this aspect of the present disclosure, the human subject is in need of pramipexole to treat a neurological disorder.

In various embodiments of this aspect of the present disclosure, the human subject is in need of pramipexole to treat a condition selected from the group consisting of Parkinson's Disease, Restless Legs Syndrome, Tourette's Syndrome, Chronic Tic Disorder, Essential Tremor, and Attention Deficit Hyperactivity Disorder.

In certain embodiments of this aspect of the present disclosure, the method comprises applying up to about 10 grams of the dosage form daily to a skin surface area of about 50 to about 500 cm².

In some embodiments of this aspect of the present disclosure, the method comprises applying the dosage form dose in a weekly single dose.

In certain embodiments of this aspect of the present disclosure, the transdermal therapeutic system applied in the method provides a rate of administration of the active ingredient(s) ranging from about 1 µg to about 200 µg per hour over seven days, e.g., from about 10 µg to about 150 µg per hour over seven days, say, from about 20 µg to about 100 µg per hour over seven days.

In yet another aspect, the present disclosure relates to a dosage form comprising pramipexole or a pharmaceutically acceptable salt thereof, wherein the dosage form provides sustained, steady-state delivery of pramipexole at a flux rate ranging from about 1 µg/cm²/hr to about 13 µg/cm²/hr for at least 48 hours after treatment is initiated.

In some embodiments of this aspect of the disclosure, the dosage form comprises pramipexole or a pharmaceutically acceptable salt thereof, wherein the dosage form provides sustained, steady-state delivery of pramipexole at a flux rate ranging from about 1 µg/cm²/hr to about 13 µg/cm²/hr for at least 48 hours after treatment is initiated.

In certain embodiments of this aspect of the disclosure, the dosage form comprises pramipexole or a pharmaceutically acceptable salt thereof, wherein the dosage form provides sustained, steady-state delivery of pramipexole at a flux rate ranging from about 1 µg/cm²/hr to about 6 µg/cm²/hr for at least 96 hours after treatment is initiated.

In various embodiments of this aspect of the disclosure, the dosage form comprises pramipexole or a pharmaceutically acceptable salt thereof, wherein the dosage form provides sustained, steady-state delivery of pramipexole at a flux rate ranging from about 1 µg/cm²/hr to about 5 µg/cm²/hr for at least 168 hours after treatment is initiated.

DETAILED DESCRIPTION

Figure 1:
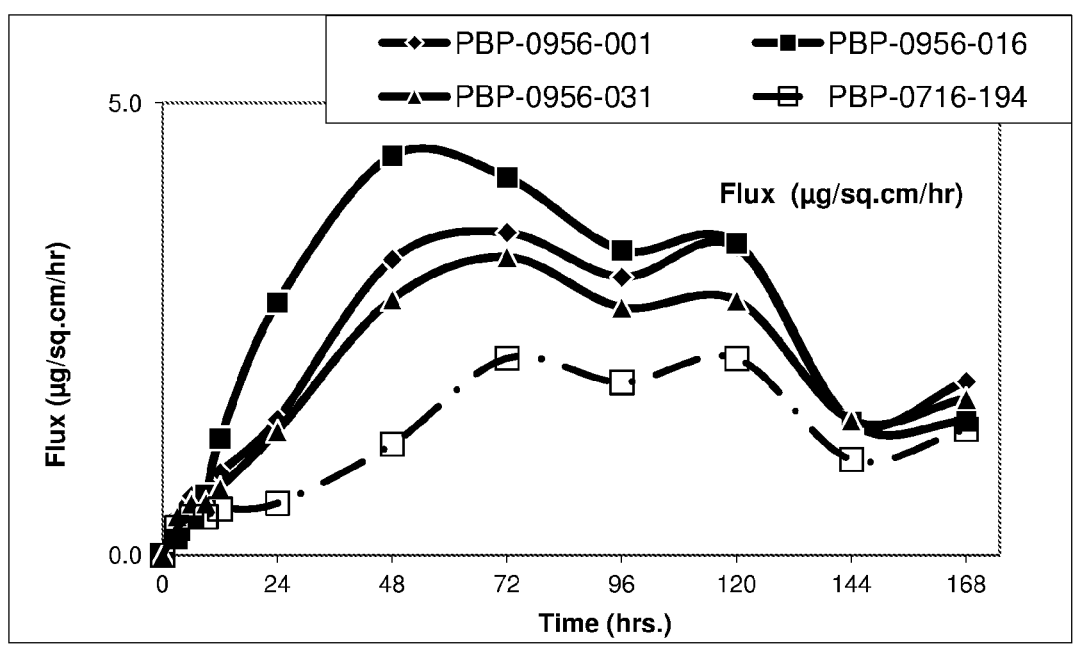
FIG. 1 depicts a flux profile which depicts flux (µg/cm²/hr) plotted over time (168 hrs) for transdermal therapeutic devices of EXAMPLES 3 and 4, which contain pramixpexole base in various matrices—acrylic-based matrices Duro-Tak™ 87-2287 and DuroTak™ 87-900 A, and silicone-based matrix Bio PSA 4301.

Current treatment options using pramipexole for Parkinsonism include conventional tablets and modified release tablets, as well as transdermal patches administered on a daily basis or more often. The present disclosure relates to the treatment of neurological disorders such as Parkinsonism using a dosage form delivering and maintaining the plasma concentration of drug over a prolonged period of time, typically two days or greater, e.g., two days, three days, four days, five days, six days, or seven days, without any need of frequent administration, using a non-invasive treatment.

The current disclosure describes the method of treatment for neurological disorders such as Parkinsonism using a transdermal therapeutic system or patch comprising a formulation of pramipexole. The presently disclosed transdermal patch can be used for once a week, twice a week, or three times a week application for the patients in need of therapy.

The components of the patch and the concentration of the drug in the patch and the dimensions of drug in adhesive layer are provided so that the patch can sustain the drug release for up to about 48 hours, about 72 hours, or about seven days or more to achieve a therapeutic plasma concentration. The treatment is non-invasive and non-irritating and ensures sufficiently constant plasma levels of the pramipexole for the intended period of treatment.

The intended transdermal patch is a drug-in-adhesive matrix type having at least three layers. In one aspect, the composition of transdermal patch consists of three distinct layers: a) a backing membrane layer; b) a drug-containing adhesive matrix layer; and c) a release liner.

The currently disclosed transdermal therapeutic system or patch contains an active ingredient in an adhesive matrix. Acrylate-based adhesives and silicone-based adhesives were found to provide both a suitable drug release profile, and a suitable stability for commercial use. Although a desirable drug release profile was observed for both acrylate- and silicone-based adhesives, the acrylate-based adhesive system was more acceptable, e.g., in terms of controlled delivery of the drug, especially for those systems in which the acrylate lacks a carboxylic acid functional group.

The current disclosure also describes transdermal therapeutic systems for the treatment of Parkinson's disease by continuous transdermal delivery of pramipexole at therapeutically relevant rates over a seven day period, making possible once-weekly dosing.

As noted, the present disclosure relates to a transdermal therapeutic system (TTS) for the administration of one or more active ingredients selected from the group consisting of pramipexole, pharmaceutically acceptable pramipexole salts, and pharmaceutically acceptable pramipexole derivatives. The system comprises: (i) a substantially active ingredient-impermeable backing layer, (ii) at least one matrix layer which contains at least about 5% w/w active ingredient(s), and (iii) a substantially impermeable protective release liner which releasably contacts the matrix layer or another adhesive layer; wherein 1) the matrix layer comprises an adhesive selected from an acrylate-based adhesive and a silicone-based adhesive, 2) the transdermal therapeutic system provides a rate of administration of the active ingredient(s) ranging from about 1 μg to about 200 μg per hour over seven days, and 3) the matrix layer is color-stable and does not promote crystal growth of the active ingredient, over an extended storage period of at least one of 30 or more days, 90 or more days, and 180 or more days.

Backing Layer

The substantially impermeable backing layer is a flexible substrate, e.g., a film or laminate, which provides support for the rest of the transdermal drug delivery device during storage, handling and wear. Any backing layer of sufficient strength and rigidity, which is substantially impermeable to the active pharmaceutical ingredient or ingredients present in the transdermal drug delivery device of the present disclosure can be used. For present purposes, "substantially impermeable" means that no substantial loss of active ingredient from the backing layer occurs under typical storage and usage conditions and periods which the device is expected to encounter during its lifetime. Typically, such losses are less than about 1 wt. %, preferably less than about 0.1 wt %, or even less than about 0.01 wt. %. The backing layer can be substantially moisture impermeable as well. Typically, a backing layer of the present disclosure has a moisture vapor transmission rate (MVTR) of less than 20 g/m²·24 hr, less than about 17 g/m²·24 hr, or less than about 15 g/m²·24 hr, e.g., from about 1 g/m²·24 hr to about 15 g/m²·24 hr, in some embodiments.

For present purposes, MVTR is defined as a measure of the passage of water vapor through a substance. It can be measured using suitable techniques. ASTM F1249 describes the procedure for MVTR testing using modulated infrared sensors which require use of a known calibration standard and determining the voltage-to-transmission-rate ratio for each sensor. Coulometric sensors for measuring oxygen transmission rates in flat films and packages, following ASTM D3985 and F1307 are also suitable and require no calibration. Typical rates in aluminum foil laminates may be as low as 0.001 g/m²/day, whereas the rate in fabrics can measure up to several thousand g/m²/day.

In various embodiments of the present disclosure, the backing layer is composed of materials that are selected from polyesters, e.g., oriented or non-oriented polyethylene terephthalate, various nylons, polypropylenes, polyester/ethylene-vinyl acetates, metallized polyester films, polyvinylidene chloride, metal films such as aluminum foils, polyvinylidene fluoride films, and mixtures or copolymers thereof.

Other non-limiting materials for the backing layer include ethylene vinyl acetate films laminated to a polyester, ethylene vinyl acetate films laminated to a metallized polyester, MEDIFLEX® 1200, MEDIFLEX® 1501, MEDIFLEX® 1505, MEDIFLEX® 1201, MEDIFLEX® 1502 (with MEDIFLEX® 1200 being especially preferred) (all five MEDIFLEX® products being available from Mylan Technologies Inc., St. Albans, Vt., USA), DuPont polyester type S available from DuPont, Wilmington, Del., USA, Dow BLF® 2050 available from The Dow Chemical Company, Midland, Mich., USA, and 3M™ Scotchpak™ 1109, 3M™ Scotchpak™ 9723, 3M™ Scotchpak™ 9733, 3M™ Scotchpak™ 9735 and 3M™ Scotchpak™ 9730, which Scotchpak™ products are available from 3M of Minneapolis, Minn., USA.

Additional materials suited for the backing layer include polyethylene or polyolefin backings, such as MEDIFLEX® 1000, 3M™ CoTran™ 9722, and 3M™ CoTran™ 9720. 3M™ CoTran™ products are available from 3M of Minneapolis, Minn., USA.

In some embodiments of the disclosure, the backing layer comprises a film selected from MEDIFLEX® 1501 (which has an MVTR of 14 g/m$^2$·24 hr), MEDIFLEX® 1000 (which has an MVTR of 7 g/m$^2$·24 hr), available from Mylan Technologies Inc., Scotchpak™ 1109, Scotchpak™ 9730, Scotchpak™ 9732, Scotchpak™ 9733, Scotchpak™ 9735, as well as CoTran™ 9719, CoTran™ 9720, and CoTran™ 9726, available from 3M. The Scotchpak™ and CoTran™ films exhibit a relatively low MVTR range of from about 0.5 to about 17 g/m$^2$·24 hr.

In certain embodiments, the backing layer is comprised of ethylene vinyl acetate or polyolefin films laminated to a polyester, such as MEDIFLEX® 1501 from Mylan Technologies, Inc. MEDIFLEX® 1501 is a three layer structure which can be described from its external surface inwardly as follows: peach-colored polyethylene/polyurethane adhesive/polyester.

In some embodiments, the backing layer may be the same size as the adhesive drug-containing layer. In other embodiments, the backing layer may be oversized as compared with the adhesive drug-containing layer, i.e., the backing layer may be larger than the adhesive drug-containing layer.

In certain embodiments of the present disclosure, the backing layer may range from about 0.01 mm to at least 10 mm larger than the matrix layer (adhesive drug-containing layer), from about 0.05 mm to about 5 mm larger than the adhesive drug-containing layer, or from about 0.1 mm to about 3 mm larger than the adhesive drug-containing layer. Without wishing to be bound by any particular theory, it is believed that the use of an oversized backing layer helps prevent the adhesive drug-containing layer and the remaining portions of the transdermal drug delivery device of the present disclosure from becoming distorted or relaxing during the handling and/or shipping processes.

The backing layer should be thick enough to resist wrinkling which may arise upon prolonged periods in storage and through the movement of a subject's skin. Typically, the backing layer is from about 50 microns to about 100 microns in thickness.

Active Ingredient-Containing Matrix Layer

An active ingredient-containing matrix layer—sometimes referred to as an adhesive drug-containing layer or drug reservoir layer—containing a therapeutically effective amount of pramipexole, its salts, and/or its derivatives, is placed directly or indirectly (through an optional intermediate layer) on the front side of the backing layer, i.e., the side toward the wearer, in the transdermal drug delivery device of the present disclosure.

For the matrix, the matrix formers customarily applied in medical applications are used, such as polyacrylates or silicone adhesives. Preferably, a self-adhesive matrix that is acrylic-based, more preferably a matrix that is based on acrylates lacking a carboxylic acid functional group, e.g., DuroTak™ 87-2287. The matrix formers and the adhesives may be one and the same.

The matrix formers based on polyacrylates may be any desired homopolymer, copolymer or terpolymer consisting of various acrylic acid derivatives, where applicable with vinyl acetate.

For example, the polyacrylates may be polymers of one or more monomers of acrylic acid and other copolymerizable monomers. In addition, the polyacrylates may include copolymers of alkyl acrylates and/or alkyl methacrylates and/or copolymerizable secondary monomers or monomers having functional groups. If the amount of any type added as monomer is altered, the cohesive properties of the resulting acrylate polymers can be altered. In general, the acrylate polymer consists of at least 50% by weight of an acrylate, methacrylate, alkyl acrylate or alkyl methacrylate monomer, from 0 to 20% by weight of a functional monomer copolymerizable with acrylate, and from 0 to 50% by weight of another monomer.

Various acrylate monomers are mentioned hereinafter, such as, for example, acrylic acid, methacrylic acid, butyl acrylate, butyl methacrylate, hexyl acrylate, hexyl methacrylate, isooctyl acrylate, isooctyl methacrylate, glycidyl methacrylate, 2-hydroxyethyl acrylate, methyl acrylate, methyl methacrylate, 2-ethylhexyl acrylate and 2-ethylhexyl methacrylate, that may be polymerized individually or in admixture.

In addition, functional monomers that are copolymerizable with the above-mentioned acrylates, such as, for example, acrylic acid, methacrylic acid, hydroxyethyl acrylate, vinyl acetate, hydroxypropyl acrylate, acrylamide, dimethylacrylamide, acrylonitrile, dimethylaminoethyl acrylate, dimethylaminoethyl methacrylate, tert.-butylaminoethyl acrylate, tert.-butylaminoethyl methacrylate, methoxyethyl acrylate and methoxyethyl methacrylate, can be used for copolymerization.

The content of adhesives in the matrix layer may be from 50 to 96% by weight, especially from 80 to 90% by weight, e.g., about 85% by weight, based on the total weight of the matrix layer.

In certain embodiments, the acrylic adhesive can be selected from the group consisting of Duro-Tak™ 87-2352, Duro-Tak™-387-2353, Duro-Tak™ 87-235A, Duro-Tak™ 387-235A, Duro-Tak™ 87-2516, Duro-Tak™-387-2526, Duro-Tak™-87-2287, Duro-Tak™ 387-2287, Duro-Tak™ 87-2194, Duro-Tak™ 387-2051, Duro-Tak™ 387-2052, Duro-Tak™ 387-2194, Duro-Tak™ 87-2196, GMS-9073, GMS-2873, GMS-9083, GMS-2883, GS-9067, GMS-9071, GMS-3083, GMS-3253, GMS-737, GMS-737-01, GMS-788, GMS-2999, GMS-2495, GMS-7883, GMS-1753, GMS-2893 and combinations thereof, or acrylic adhesives having substantially the same composition as these materials. The Duro-Tak™ products are available from Henkel of Dusseldorf, Germany and can be characterized as containing acrylic copolymers. GMS products are available from the Cytec Corporation, Germany.

In certain embodiments, cross-linkable adhesives useful in making the matrix layer of the present disclosure include medical grade acrylic cross-linkable adhesives. As used herein, "cross-linkable adhesive" refers to an adhesive provided as a solvent-based solution that contains a cross-linking agent. As provided, the adhesive is uncross-linked; when the solution is dried to remove the solvent, the cross-linker is activated and the cross-linking of the adhesive occurs. Suitable acrylic adhesives include acrylate-vinylacetate self-curing pressure sensitive adhesives, such as Duro-Tak™ 387-2516/87-2516.

In some embodiments, non-cross-linkable acrylic adhesive can be used to make the matrix layer. As used herein, a "non-cross-linkable adhesive" refers to an adhesive provided as a solvent-based solution that does not contain a cross-linking agent. Examples of non-cross-linkable adhesive are acrylate-vinylacetate non-curing PSAs Duro-Tak™ 387-2287 and Duro-Tak™ 87-2287, as well as mixtures thereof.

In certain embodiments of the disclosure, a mixture of the above cross-linkable adhesive and non-cross-linkable adhesive may be used to make the matrix layer. Prior to drying, the cross-linkable acrylic adhesive is mixed with a second, non-cross-linkable adhesive. Preferably, the solution of non-cross-linkable adhesive comprises the same polymer as provided in the solution of the cross-linkable adhesive. Thus, if the cross-linkable adhesive comprises Duro-Tak™ 387-2516 and/or Duro-Tak™ 87-2516, then the non-cross-linkable adhesive comprises Duro-Tak™ 387-2287, Duro-Tak™ 87-2287. See, e.g., U.S. Published Application Number 2011/0106022 to Jackson et al.

In certain embodiments of the disclosure, the acrylic pressure-sensitive adhesive can comprise a random copolymer of 2-ethylhexyl acrylate, butyl acrylate, t-octyl acrylamide and methyl methacrylate. In these embodiments, the adhesive may have a composition that is substantially the same as the composition of Duro-Tak™ 87-900 A (available from Henkel of Dusseldorf, Germany or National Adhesives, Bridgewater, N.J.). The term "substantially the same" as used herein refers to a composition that is a copolymer of 2-ethylhexyl acrylate, butyl acrylate, t-octyl acrylamide and methyl methacrylate and provides for the storage stable functionality as described above. In some embodiments, the acrylic pressure-sensitive adhesive is Duro-Tak™ 87-900 A itself.

In various embodiments of the present disclosure, the acrylic adhesive comprises acrylate co-polymer, e.g. co-polymer of butyl acrylate, ethyl hexyl acrylate and vinyl acetate. The co-polymer can be cross-linked. A preferred acrylate polymer can be selected from the Duro-Tak™ brand, e.g. Duro-Tak™ 87-2353. Duro-Tak™ 87-235A is particularly advantageous inasmuch as it lacks the monomer glycidyl methacrylate component found in Duro-Tak™ 87-2353.

The acrylic adhesive layer can be attached or adjacent to a backing film directly or through a suitable intermediate layer. In certain embodiments of the present disclosure, the acrylic adhesives used in the intermediate layer are selected from Duro-Tak™ 87-2352, Duro-Tak™ 387-2353, Duro-Tak™ 87-235A, Duro-Tak™ 387-2351, Duro-Tak™ 87-2516, Duro-Tak™ 387-2526, Duro-Tak™ 87-2287, Duro-Tak™ 387-2287, Duro-Tak™ 87-2194, Duro-Tak™ 387-2194, Duro-Tak™ 87-2196 and combinations thereof.

In some embodiments, the matrix layer comprises suitable silicone adhesives alone or with the above-described acrylic adhesives. The silicone adhesives include pressure sensitive adhesives made from silicone polymer and resin. The polymer to resin ratio can be varied to achieve different levels of tack, which is useful where the matrix layer is the skin contact layer of a device of the present disclosure. Specific examples of useful silicone adhesives for this purpose which are commercially available include the standard Dow Corning® BIO-PSA series (7-4400, 7-4500 and 7-4600 series) and the amine compatible (endcapped) Dow Corning® BIO-PSA series (7-4100, 7-4200 and 7-4300 series) manufactured by Dow Corning. Preferred adhesives include Dow Corning® BIO-PSA 7-4201, 7-4202, 7-4301, 7-4302, 7-4501, 7-4502 and 7-4602, with BIO-PSA 7-4201, BIO-PSA 7-4301, BIO-PSA 7-4302 or mixtures thereof, e.g., BIO-PSA 7-4201, BIO-PSA 7-4301 and/or BIO-PSA 7-4302 being especially preferred.

In certain embodiments, the skin-contact layer contains an active pharmaceutical ingredient (API), where the API itself and degree of saturation of API in this layer is about the same as the degree of saturation in the adhesive layer.

In some embodiments, the skin-contact layer contains one or more additives, e.g., a tackifier. A tackifier is added to provide a desired stickiness to the product, typically a stickiness sufficient to adhere the device to a patient's skin, without the patient feeling undue discomfort upon removal of the device. Tack can be measured by conventional techniques such as the Instron Peel Strength Test or the "Tel-Tak" test, employing a tackmeter sold by Monsanto Co., Testing Instruments Division.

In various embodiments of the present disclosure, the optional tackifier can also be present in the adhesive drug-containing layer, typically in amounts ranging from about 10 wt. % to about 30 wt. %, e.g., from about 15 wt. % to about 25 wt. %, e.g., from about 17 wt. % to about 23 wt. %, typically, about 20 wt. %. The tackifier can be a suitable silicone oil, e.g., polydimethyl siloxane, such as Dow Corning® Medical Fluid, 12,500 cSt.

In some embodiments of the present disclosure, the matrix layer can contain one or more optional solubilizers and/or crystal growth inhibitors. Suitable active ingredient solubilizers and/or active ingredient crystal growth inhibitors can include optionally saturated and/or unsaturated fatty alcohols each containing from 8 to 18 carbon atoms; tea tree oil; saturated and/or unsaturated cyclic ketones; alkyl methyl sulfoxides; saturated and/or unsaturated fatty acids each containing from 8 to 18 carbon atoms; esters and salts thereof; natural vitamin E (Copherol® F1300); synthetic vitamin E and/or vitamin E derivatives; sorbitan fatty acid esters and/or ethoxylated sorbitan fatty acid esters; azones (laurocapram); 1-alkylpyrrolidone; polyvinylpyrrolidone; block copolymers of polyethylene glycol and dimethylsiloxane with a cationic group at one end; polysiloxanes; polyoxyethylene-10-stearyl ether; mixture of polyoxyethylene-10-stearyl ether and glyceryl dilaurate; dodecyl-2-(N,N-dimethylamino)-propanol tetradecanoate and/or dodecyl-2-(N,N-dimethylamino)-propionate; N-acetylprolinate esters with >8 carbon atoms; non-ionic surfactants, for example lauryl ethers and/or esters of polyoxyethylene; dimethyl(arylimino)sulfuran; mixture of oleic acid analogues and propylene glycol; mixture of octyl salicylate, isopropyl myristate, isopropyl palmitate, octylmethoxy cinnamate and laurocapram or a mixture of individual components; phospholipids; highly dispersed silicon dioxide (Aerosil®); polyoxyethylene-7-glycerol monococoate (Cetiol® HE); 2-octyldodecanol (Eutanol® G) or a mixture of various individual components. Povidone (polyvinylpyrrolidone) is preferred as the solubilizer and/or active ingredient crystal growth inhibitor in the transdermal therapeutic system according to the invention.

In certain embodiments of the present disclosure, the transdermal drug delivery device comprises plural or multiple adhesive drug-containing layers, e.g., adhesive bilayers, trilayers, quadrilayer, pentalayers, etc., which include an acrylic adhesive matrix layer or silicone adhesive matrix layer, and a skin contact layer. The skin contact layer can be directly attached to the acrylic adhesive matrix layer or silicone adhesive matrix layer, or alternately, is attached to an intermediate membrane layer placed between the adhesive matrix layer and the skin contact layer. In plural or multiple adhesive drug-containing layer embodiments of the present disclosure, a skin contact layer is typically present in addition to a separate adhesive layer as described above. In some embodiments the skin contact layer itself contains an active pharmaceutical ingredient. In other embodiments, no active pharmaceutical ingredient is present in the skin contact layer.

An optional skin contact layer adjacent to the adhesive drug containing layer or matrix layer comprises a skin contact layer adhesive, an optional drug component, usually of the type already present in the adhesive layer, and an optional tackifier. The adhesive is selected from silicones, including silicone oils, e.g., "medical fluids," natural and synthetic rubbers, polyisobutylene ("PIB") (HMW (High Molecular Weight) PIB, LMW (Low Molecular Weight) PIB, or mixtures of HMW and LMW PIB), neoprenes, polybutadienes, polyisoprenes, polysiloxanes, acrylic adhesives including cross-linked and uncross-linked acrylic copolymers, vinyl acetate adhesives, polyacrylates, ethylene vinyl acetate copolymers, styrene-isoprene copolymers, polyurethanes, plasticized polyether block amide copolymers, plasticized styrene-rubber block copolymers, and mixtures thereof.

TABLE 1 below sets out desirable ranges of ingredients for the active ingredient-containing layer of the transdermal therapeutic system of the present disclosure which utilizes an acrylic matrix layer (Duro-Tak™ 87-287).

TABLE 1

Acrylate PSA system - DuroTak 87-2287

| Ingredients | Workable range % w/w concentration | Preferred Range % w/w concentration | Preferred composition |
|---|---|---|---|
| Pramipexole Base | 4.5-7.0 | 5.0-6.0 | 5.5 |
| DuroTak 87-2287 | 65.0-96.0 | 80.0-95.0 | 84.5 |
| PVP (Plasdone) K 90 | 0-15.0 | 2.5-10.0 | 10.0 |
| Ethanol | qs | qs | qs |

Thickness of Adhesive Layer: 70-100 gsm
Patch size: 50 cm$^2$

TABLE 2 below sets out desirable ranges of ingredients for the active ingredient-containing layer of the transdermal therapeutic system of the present disclosure which utilizes an acrylic matrix layer (Duro-Tak™ 87-900A).

TABLE 2

Acrylate PSA system - DuroTak 87-900 A

| Ingredients | Workable range % w/w concentration | Preferred Range % w/w concentration | Preferred composition |
|---|---|---|---|
| Pramipexole Base | 4.5-9.0 | 5.0-6.0 | 5.5 |
| DuroTak 87-900 A | 65.0-96.0 | 80.0-95.0 | 84.5 |
| PVP (Plasdone) K 90 | 0-15.0 | 2.5-10.0 | 10.0 |
| Ethanol | qs | qs | qs |

Thickness of Adhesive Layer: 70-100 g/m$^2$
Patch size: 50 cm$^2$

TABLE 3 below sets out desirable ranges of ingredients for the active ingredient-containing layer of the transdermal therapeutic system of the present disclosure.

TABLE 3

Silicone BIO PSA Adhesive system - 4301

| Ingredients | Workable range % w/w concentration | Preferred Range % w/w concentration | Preferred composition |
|---|---|---|---|
| Pramipexole Base | 4.5-9.0 | 6.0-7.0 | 6.0 |
| Bio PSA 4301/4201 | 65.0-96.0 | 80.0-94.0 | 85.5 |
| Silicone Oil | 0-10.0 | 0-10.0 | 5.0 |
| Colloidal silicone dioxide | 0-5.0 | 0-5.0 | 2.5 |
| n- Heptane | qs | qs | qs |

Thickness of Adhesive Layer: 70-100 g/m$^2$
Patch size: 50 cm$^2$

Release Liner Layer

Substantially impermeable protective release liners which are well known in the art can be used for the release liner layer of the present disclosure, especially where they exhibit adequate moisture impermeability. For present purposes, "substantially impermeable" means that no substantial loss of active ingredient from the release liner occurs under typical storage and usage conditions and periods which the device is expected to encounter during its lifetime. Typically, such losses are less than about 1 wt. %, preferably less than about 0.1 wt %, or even less than about 0.01 wt. %. The release liner layer can be substantially moisture impermeable as well. For present purposes, the substantially impermeable release liner layer is a flexible substrate, e.g., a film or laminate, which is releasably secured to the skin contact layer, e.g., a peelable layer. The release liner layer serves to protect the adhesive surface of the layer of the device which is to be applied to a subject's skin, e.g., during storage and any other time prior to use of the device. Any release liner layer of sufficient strength and rigidity, and which is substantially moisture impermeable, is suited for use in the present disclosure. Typically, such a release liner layer has a moisture vapor transmission rate (MVTR) of less than 20 g/m$^2$·24 hr, e.g., less than about 17 g/m$^2$·24 hr, e.g., from about 1 g/m$^2$·24 hr g/m$^2$/24 hr to about 15 g/m$^2$·24 hr. MVTR can be measured for the release liner layer in the same way as earlier described in relation to the backing layer.

Non-limiting examples of materials from which the release liner layer may be composed include polyethylene terephthalate/silicone (i.e. polydimethyl siloxane or "PET/SI"), polyethylene terephthalate/aluminized polyester coated with silicone (i.e. polydimethyl siloxane or "PET/MET/SI"), polyester or polyurethane liners with a silicone coating, polyester or polyurethane liners with a fluorocarbon or fluorosilicone coating, e.g., a polyfluoroalkylsiloxane, or polyester or polyurethane liners with a silicone coating.

In various embodiments, the protective release liner layer comprises fluorosilicone coated polyester or silicone coated polyester. Suitable release liners include polyester film and polypropylene film coated with a fluoropolymer release agent. Such release liner layers include Scotchpak™ 1020, 1022, 9741, 9742, 9744 and 9755 available from 3M, of which Scotchpak™ 1022 is especially preferred. Other suitable release liner constituents include MEDIRELEASE® 2500, MEDIRELEASE® 2249 and MEDIRELEASE® 2226, each of which is available from Mylan Technologies, Inc., of which MEDIRELEASE® 2249 can be especially preferred. Still other suitable release liner layers can be made from CPFilms Inc. Clearsil® UV5A and CPFilms Inc., Clearsil® UV510, CPFilms Inc. Sil® UV5A and CPFilms Inc. Sil® UV510, which are available from CPFilms, Inc. of Fieldale, Va., USA.

The release liner layer can, however, comprise other materials, including paper or paper-containing layers or laminates, various thermoplastics, polyester films, foil liners, and the like. The release liner is removed and discarded from the transdermal delivery device to expose the skin contact adhesive layer which functions as the means of adhering the composition to the patient and through which the drug passes as it is delivered to the patient. Suitable release liners include those known in the art for use with pressure sensitive adhesive compositions.

In some embodiments, the release liner layer may be the same size as the matrix layer and/or may be the same size as the backing layer. In any event, the release liner should be at least coextensive with the surface of the matrix layer, in order to prevent migration of the active component prior to release liner removal. In other embodiments, the release liner layer may be larger than the adhesive matrix layer and/or may be larger than the backing layer. In yet other embodiments, the release liner may range from about 0.1 mm to at least about 20 mm larger than the margin of a backing layer or a matrix layer, preferably ranging from about 0.5 mm to about 10 mm larger than the backing layer or matrix layer, and most preferably ranging from about 1 mm to about 5 mm larger than the backing layer or matrix layer. It is believed that the use of an oversized release liner facilitates its removal by the user prior to application to the skin and also helps prevent the matrix from becoming distorted or relaxing during the handling and shipping processes. In certain embodiments, the release liner layer is of square or rectangular shape and can be attached to a smaller patch, e.g., one of circular shape.

Methods of Preparing Transdermal Therapeutic System (Dosage Unit Forms)

The transdermal therapeutic system drug delivery devices of this disclosure can be made by first preparing separate adhesive blends for each layer of the dosage unit, then dissolving or suspending the drug of choice in at least one of the blends, each of which has been made by mixing a suitable solvent with the pressure sensitive adhesive of choice. The drug reservoir layer can be coated first on a release liner, dried and then laminated to the desired backing film, according to predetermined parameters, such as temperature and dwell time (line speed), which yield minimal residual solvent levels. The optional skin contact layer can then be coated on a separate release liner and dried. The release liner can be removed from the drug reservoir layer and the adhesive side of the skin contact layer laminated onto the adhesive side of the drug reservoir layer so that the drug reservoir layer lies between the backing and the skin contact layer. If the drug initially is suspended or dissolved in only one of the two adhesive layers, it will, over time, equilibrate into the other adhesive layer until the degree of saturation is the same in both layers. It may be desirable to prepare the composition with the drug initially suspended or dispersed in only one of the two adhesive layers if for example, the other adhesive layer is prepared with a solvent which would be deleterious to the drug but which evaporates during processing (coating and drying).

If more than two layers are to be provided, the third (middle) layer can be coated as a liquid onto a release liner, dried, laminated to either the adhesive side of the dried skin contact layer or the adhesive side of the dried drug reservoir layer once the release liner has been removed from the latter. Then the two parts of the dosage unit can be laminated to one another as above.

Suitable solvents for use in preparing the adhesive blends include acetone, heptane, ethyl acetate, isopropanol, ethanol, hexane, toluene, xylene, 2,4-pentanedione, methanol and water. Short-chain alcohols such as methanol, ethanol, n-propanol, iso-propanol, n-butanol, iso-butanol and tert-butanol are preferred, especially for use with acrylic-based matrix. Ethanol is especially preferred. Alkanes such as heptanes, e.g., n-heptane and hexanes, e.g., n-hexane, are especially preferred for use with silicone-based matrices.

Alternative methods for producing or achieving a transdermal delivery dosage unit in accordance with this invention may be apparent to persons skilled in the art, and such alternative methods also fall within the scope of the present invention. For example, an adhesive blend can be coated onto the backing film rather than the release liner. Alternatively, an adhesive coating can be created without using a solvent, such as by heating a hot-melt adhesive to its melting temperature. With this technique, no drying of the adhesive is required, only cooling.

There are many coating techniques for applying a continuous liquid coating onto a substrate, including using a gravure roll, reverse roll, falling film, inkjet, etc. All of these are well-known to persons of ordinary skill in the art and can be used to create pressure-sensitive adhesive layers from a fluid blend. Alternatively, a thin adhesive coating can be achieved by extrusion, in which the adhesive blend is forced through a die under pressure onto the substrate either as a continuous coating or as a printed (intermittent) pattern.

The thickness of the adhesive drug-containing layer (drug reservoir layer) and optional skin contact layers of the compositions of this invention can vary, depending upon such factors as the amount of drug to be delivered from the composition and the desired wear period.

Although such processes can be used for any sized patch, it is particularly suited for use in patches having a surface area ranging from between about 5 $cm^2$ and about 100 $cm^2$, and preferably ranging from between about 25 $cm^2$ and about 75 $cm^2$, e.g., a patch having a surface area of about 50 $cm^2$.

In various embodiments of the disclosure, the patches are of any suitable thickness, e.g., about 20 microns or greater in total thickness, including the release liner layer. Certain embodiments of the disclosure range from between about 20 microns to about 1,500 microns in total thickness. In some embodiments, the patches have a total thickness of about 250 microns.

The dosage unit forms are made from the resulting multiple layer structure by die stamping to provide patches of desired shape and size.

Once the dosage unit forms have been prepared, they are placed in an appropriate packaging system for storage and sealed therein in the substantial absence of oxidizing agents, e.g., air, until they are to be used in transdermal treatment. The packaging system can comprise a pouch, envelope, or any other suitable structure surrounding the dosage unit form. The structure is typically made from a plastic film or laminated film which is substantially impermeable to water vapor and air, including oxygen. In various embodiments the laminate can comprise a thermoplastic film which is heat sealable.

In certain embodiments the packaging system comprises a pouch made from a multiple laminate film. The film typically exhibits an oxygen transmission rate of less than about 0.05 ml/100 $in^2$/24 hr/bar measured at 22° C. (72° F.), e.g., less than about 0.04 ml/100 $in^2$/24 hr/bar measured at 22° C. (72° F.), e.g., from about 0.01 to about 0.03 ml/100 $in^2$/24 hr/bar.

Once the dosage unit forms have been prepared, they are placed and sealed in appropriate packaging for storage until they are to be applied in transdermal treatment.

The compositions of this disclosure possess sufficient adhesive properties that once the release liner is removed and the composition is applied to a patient's skin the composition can remain in place for a period of time sufficient to distribute the desired amount of the drug contained therein with a low incidence of debonding or delamination.

In certain embodiments of the present disclosure, the thickness of the matrix layer or pharmaceutical composition layer in the transdermal device of the present disclosure ranges from about 20 to about 1000 microns, more preferably from about 60 to about 100 microns.

In various embodiments of the present disclosure, the transdermal device is formed as a continuous sheet or web and may be cut into desired width and length, or separated along a frangible area dividing each device, into patches before use although such devices may be provided as discrete patches which are cut with a die into the desired shape, e.g., circular.

The transdermal devices of the invention in general have, for example an effective contact area of pharmaceutical composition on the skin of from about 1 to about 80 cm$^2$, preferably about 50 cm$^2$, and are intended to be applied at intervals of about once every 2 to 7 days, preferably about every 7 days. The patch may be applied, for example on the abdomen, thigh, behind an ear, or on a shoulder or upper arm.

Pharmaceutical compositions of the present disclosure formed as a transdermal device are useful for the same indications as for known compositions containing the active pharmaceutical ingredient or drug. The exact amounts of active pharmaceutical ingredient to be administered may depend on a number of factors, e.g. the drug release characteristics of the compositions, the drug penetration rate observed in vitro and in vivo, the duration of action required, the form of active pharmaceutical ingredient, and for transdermal compositions the size of the skin contact area, and the part of the body to which the unit is fixed. The amount of active pharmaceutical ingredient and surface area of the patch may be optimized through routine bioavailability tests measuring the blood levels of active agents after administration of the active pharmaceutical ingredient composition to intact skin and comparing those blood levels to those following oral administration of a therapeutically effective dose of the active pharmaceutical ingredient.

With reference to the FIGURES, the transdermal device of the present disclosure can be further explained as follows:

FIG. 1 depicts a flux profile which depicts flux (μg/cm$^2$/hr) plotted over time (168 hrs) for transdermal therapeutic devices which contain pramixpexole base in various matrices—acrylic-based matrices DuroTak™ 87-2287 and Duro-Tak™ 87-900 A, and silicone-based matrix Bio PSA 4301.

Figure 2:
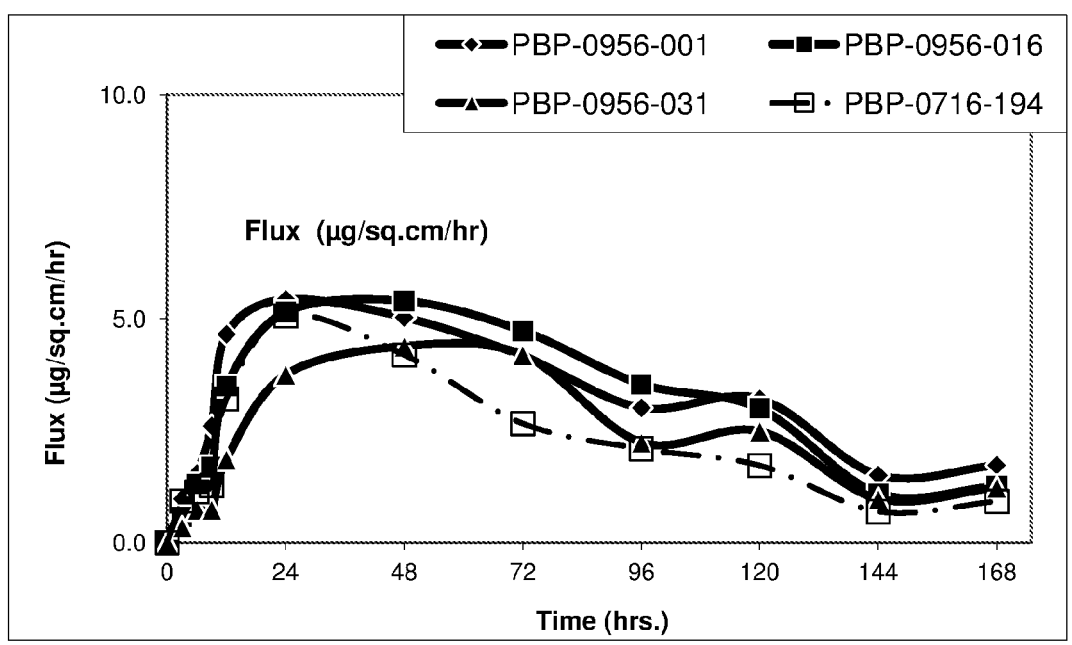
FIG. 2 depicts a flux profile which depicts flux (µg/cm²/hr) plotted over time (168 hrs) for transdermal therapeutic devices of EXAMPLES 3 and 4, which contain pramixpexole base in various matrices—acrylic-based matrices Duro-Tak™ 87-2287 and DuroTak™ 87-900 A, and silicone-based matrix Bio PSA 4301.

FIG. 2 depicts a flux profile which depicts flux (μg/cm$^2$/hr) plotted over time (168 hrs) for transdermal therapeutic devices which contain pramixpexole base in various matrices—acrylic-based matrices DuroTak™ 87-2287 and Duro-Tak™ 87-900 A, and silicone-based matrix Bio PSA 4301.

Figure 3:
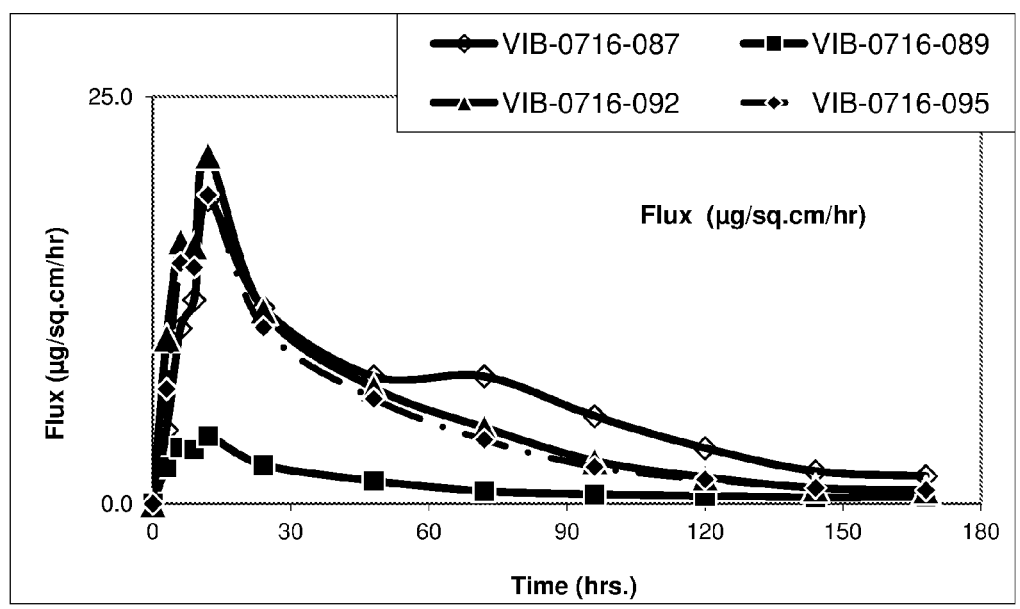
FIG. 3 depicts a flux profile which depicts flux (µg/cm²/hr) plotted over time (168 hrs) for transdermal therapeutic devices of EXAMPLES 5-8, which contain pramipexole base in various matrices—silicone-based matrix Bio PSA 4301, polyisobutylene-based matrix, and acrylic matrix-based DuroTak™ 87-2287.

FIG. 3 depicts a flux profile which depicts flux (μg/cm$^2$/hr) plotted over time (168 hrs) for transdermal therapeutic devices which contain pramixpexole base in various matrices—silicone-based matrix Bio PSA 4301, polyisobutylene-based matrix, and acrylic matrix-based DuroTak™ 87-2287.

Figure 4:
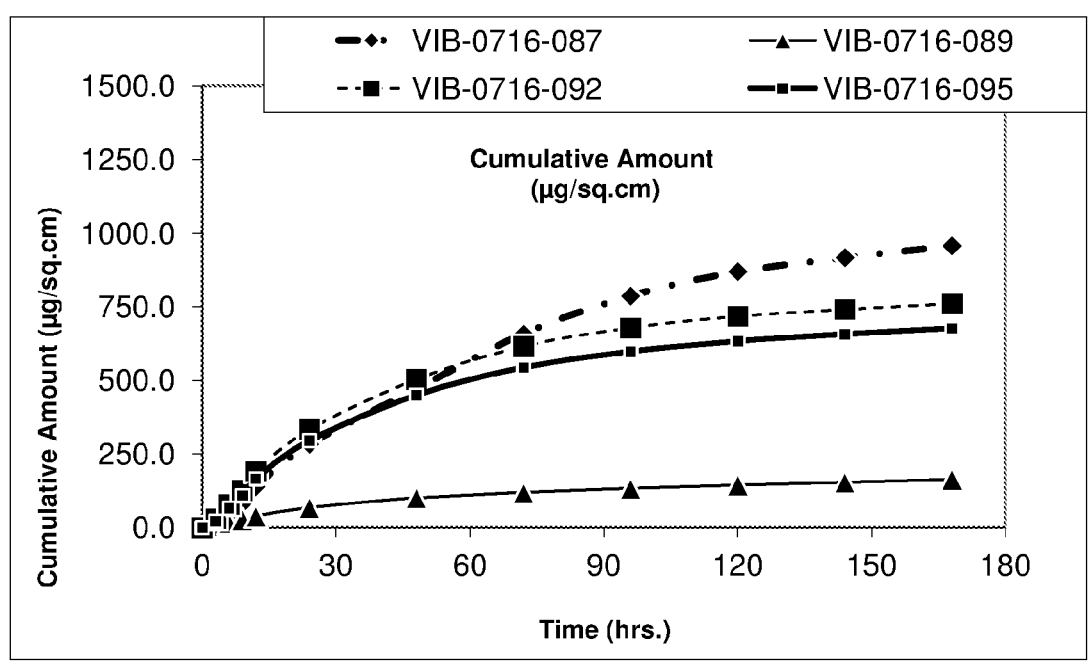
FIG. 4 depicts cumulative flux profile which depicts flux (µg/cm²) plotted over time (168 hrs) for transdermal therapeutic devices of EXAMPLES 5-8.

FIG. 4 depicts a diagram of the product of the present disclosure showing i) a backing film as the upper layer, ii) an intermediate layer comprising a monolithic adhesive matrix which comprises 1) acrylic adhesive or silicone adhesive, 2) active pharmaceutical ingredient, e.g., pramipexole free base, and 3) crystal growth inhibitor, e.g., polyvinylpyrrolidone, and iii) a lower layer comprising a protective release liner which can be slit or scored to permit easy removal of the liner, in two parts, from the rest of the product.

The invention will now be described in more detail by the following non-limiting EXAMPLES. In all the EXAMPLES, the polymer matrix contains the active pharmaceutical ingredient pramipexole free base in an amount of at least 5.5% w/w relative to the active-containing matrix. The EXAMPLES are presented to illustrate but a few embodiments of the invention. All parts are by weight unless otherwise indicated.

Examples 1-4 (Acrylic-Based Samples)

Four samples of the transdermal therapeutic system of the present disclosure were prepared as follows, based on the batch compositions used in preparing the active ingredient-containing matrix layers (acrylic-based), two with Duro-Tak™ 87-900 A and two with Duro-Tak™ 87-2287 A as set out in TABLE 4 below.

TABLE 4

| | Batch | | | |
|---|---|---|---|---|
| | Batch compositions using Duro-Tak™ 87-900 A | | Batch compositions using Duro-Tak™ 87-2287 A | |
| Ingredient | Ex. 1 % w/w | Ex. 2 % w/w | Ex. 3 % w/w | Ex. 4 % w/w |
| Pramipexole free base | 5.5 | 6.0 | 5.5 | 6.0 |
| Plasdone K-90 (Polyvinylpyrrolidone) | 5.0 | 10.0 | 5.0 | 10.0 |
| Duro-Tak™ 87-2287 A | — | — | 89.5 | 84 |
| Duro-Tak™ 900 A | 89.5 | 84 | — | — |
| Ethanol | q.s. | q.s. | q.s. | q.s. |

Ethanol was added to a glass beaker to which polyvinylpyrrolidone (povidone) Plasdone™ K-90, available from Ashland, Inc. was added and dissolved. Pramipexole free base was then added to the beaker and dissolved by sonication to form a pramipexole mixture. The Duro-Tak™ component was then weighed in a glass jar to which was then added the pramipexole mixture with mixing for a suitable time using a stirrer and/or jar roller. The jar rolling was carried out as needed to effectively degas the resulting mixture. The resulting degassed matrix layer precursor mixture was then coated onto one side of a MEDIRELEASE® 2249 film. The uncoated side was then laminated with MEDIFLEX® 1200 backing layer.

Example 5 (Silicone-Based Sample)

A sample of the transdermal therapeutic system of the present disclosure was prepared as follows, based on the batch composition used in preparing the active ingredient-containing matrix layer (silicone-based), made with Bio PSA 7-4301 as set out in TABLE 5 below.

TABLE 5

| Ex. 5 - Batch composition using Silicone Bio PSA | |
|---|---|
| Ingredient | % w/w |
| Pramipexole base | 7.0 |
| Silicone (Bio PSA 7-4301) | 93.0 |

DOW CORNING® BIO-PSA 7-4301 SILICONE ADHESIVE was weighed out and added to a glass jar, to which a weighed portion of pramipexole free base was then added and dispersed to form a pramipexole mixture, followed by mixing for a suitable time using a stirrer and/or jar roller. The jar rolling was carried out as needed to effectively degas the resulting mixture. The resulting degassed matrix layer precursor mixture was coated onto one side of a Scotchpak™ 1022 release film layer. The uncoated side was then laminated with MEDIFLEX® 1200 backing layer.

Example 6 (Comparative Polyisobutene-Based Sample)

A sample of the transdermal therapeutic system of the present disclosure was prepared as follows, based on the batch composition used in preparing the active ingredient-containing matrix layer (silicone-based), made with Duro-Tak™ PIB 612 A as set out in TABLE 6 below.

TABLE 6

| Ex. 6 - Drug Composition Using Polyisobutene Adhesive | |
|---|---|
| Ingredient | % w/w |
| Pramipexole base | 7.0 |
| Duro-Tak™ PIB 612 A | 93.0 |

Duro-Tak™ PIB 612 A polyisobutene adhesive was weighed out and added to a glass jar, to which a weighed portion of pramipexole free base was then added and dispersed to form a pramipexole mixture, followed by mixing for a suitable time using a stirrer and/or jar roller. The jar rolling was carried out as needed to effectively degas the resulting mixture. The resulting degassed matrix layer precursor mixture was coated onto one side of a Scotchpak™ 1022 release film layer. The uncoated side was then laminated with MEDIFLEX® 1200 backing layer.

Example 7 (Multi-Layer Adhesive Matrix without Polyvinylpyrrolidone)

A sample of the transdermal therapeutic system of the present disclosure was prepared as follows, based on the batch composition used in preparing the active ingredient-containing matrix layers (including a skin contact layer without active ingredient), made with Duro-Tak™ 87-2287 A as set out in TABLE 7 below.

TABLE 7

| Ex. 7 - Drug Composition Using Multi-Layer Adhesive Matrix | |
|---|---|
| Ingredient | % w/w |
| Pramipexole base | 7.0 |
| Duro-Tak™ 87-2287 A | 93.0 |
| Ethanol | q.s. |
| Contact layer (Without Drug) | |
| Duro-Tak™ 87-2287 A | 100.0 |

Ethanol was weighed and added to a glass beaker. Pramipexole free base was then added to the beaker and dissolved to form a pramipexole mixture. The Duro-Tak™ component was then weighed in a glass jar to which was then added the pramipexole mixture with mixing for a suitable time using a stirrer and/or jar roller. The jar rolling was carried out for a suitable time as needed to effectively degas the resulting mixture. The resulting degassed matrix layer precursor mixture was then coated onto one side of a MEDIRELEASE® 2249 film. The uncoated side was then laminated with MEDIFLEX® 1200 backing layer. The contact layer was prepared by coating one side of a MEDIRELEASE® 2249 film with Duro-Tak™ 87-2287 A. The release liner was then removed from the pramipexole-containing laminate and laminated with the contact layer, providing a multi-layer adhesive matrix having a skin contact layer.

Example 8 (Multi-Layer Adhesive Matrix with Polyvinylpyrrolidone)

A sample of the transdermal therapeutic system of the present disclosure was prepared as follows, based on the batch composition used in preparing the active ingredient-containing matrix layers (including a skin contact layer without active ingredient), made with Duro-Tak™ 87-2287 A as set out in TABLE 8 below.

TABLE 8

| Ex. 8 - Drug Composition Using Multi-Layer Adhesive Matrix | |
|---|---|
| Pramipexole base | 7.0 |
| Duro-Tak™ 87-2287 A | 88.0 |
| Plasdone K-90 (Polyvinylpyrrolidone) | 5.0 |
| Ethanol | q.s. |
| Contact layer | |
| Duro-Tak™ 87-2287 A | 100.0 |

Ethanol was added to a glass beaker to which polyvinylpyrrolidone (povidone) Plasdone™ K-90, available from Ashland, Inc. was added and dissolved. Pramipexole free base was then weighed out, added to the beaker and dissolved by sonication to form a pramipexole mixture. The Duro-Tak™ component was then weighed in a glass jar to which was then added the pramipexole mixture with mixing for a suitable time using a stirrer and/or jar roller. The jar rolling was carried out for a suitable time as needed to effectively degas the resulting mixture. The resulting degassed matrix layer precursor mixture was then coated onto one side of a MEDIRELEASE® 2249 film. The uncoated side was then laminated with MEDIFLEX® 1200 backing layer. The contact layer was prepared by coating one side of a MEDIRELEASE® 2249 film with Duro-Tak™ 87-2287 A. The release liner was then removed from the pramipexole-containing laminate and laminated with the contact layer, providing a multi-layer adhesive matrix having a skin contact layer.

Example 9 (Crystal Growth Observation for Batch Composition Using Duro-Tak™ 87-900A)

A product of the disclosure made from a batch composition using Duro-Tak™ 87-900A was inspected for appearance, including color and crystal growth. It was then separately subjected to storage for six months at accelerated aging conditions (40° C.) and control room temperature conditions (20° C.) and then reinspected. Results are set out below in TABLE 9.

TABLE 9

Batch Compositions Using Duro-Tak™ 87-900A

| Parameters | Initial | 6 Months |
|---|---|---|
| Appearance | Clear translucent patches | Clear translucent patches No color change observed |
| Crystal growth | | |
| accelerated aging condition | Clear translucent patches | Clear translucent patches No crystal growth observed |
| Control room temperature. | Clear translucent patches | Clear translucent patches No crystal growth observed |

Example 10 (Crystal Growth Observation for Batch Composition Using Duro-Tak™ 87-2287 A)

A product of the disclosure made from a batch composition using Duro-Tak™ 87-2287 A was inspected for appearance, including color and crystal growth. It was then separately subjected to storage for six months at accelerated aging conditions (40° C.) and control room temperature conditions (40° C.) and then reinspected. Results are set out below in TABLE 10.

TABLE 10

Batch Compositions Using Duro-Tak™ 87-2287 A

| Parameters | Initial | 6 Months |
|---|---|---|
| Appearance | Clear translucent patches | Clear translucent patches No color change observed. |
| Crystal growth | | |
| Accelerated aging condition | Clear translucent patches | Clear translucent patches No crystal growth observed. |
| Control room temperature. | Clear translucent patches | Clear translucent patches No crystal growth observed. |

Example 11 (Crystal Growth Observation for Batch Compositions Using Silicone Adhesive and Polyisobutene Adhesive)

Products made from batch compositions using Dow Corning® BIO-PSA 7-4301 (Silicone Adhesive) and Duro-Tak™ PIB 612 A (Polyisobutene Adhesive) were inspected for appearance, including color and crystal growth. They were then separately subjected to storage for six months at accelerated aging conditions (40° C.) and control room temperature conditions (20° C.) and then reinspected. The results are set out below in TABLE 11.

TABLE 11

Batch compositions using Dow Corning® BIO-PSA 7-4301 (Silicone Adhesive) and Duro-Tak™ PIB 612 A (Polyisobutene Adhesive)

| Parameters | Initial | 6 Months |
|---|---|---|
| Appearance | Translucent patches with drug dispersed in adhesive matrix | Translucent patches with drug dispersed in adhesive matrix. No color change observed. |
| Crystal growth | | |
| accelerated condition | Translucent patches with drug dispersed in adhesive matrix | Translucent patches with drug dispersed in adhesive matrix. No crystal growth or agglomerates observed. |
| Control room temperature | Translucent patches with drug dispersed in adhesive matrix | Translucent patches with drug dispersed in adhesive matrix No crystal growth or agglomerates observed |

Example 12 (Stability Testing for Batch Composition Using Duro-Tak™ 87-900A)

A product of the disclosure made from a batch composition using Duro-Tak™ 87-900A was tested for initial stability including the presence of crystals and impurities associated with pramipexole manufacture and degradation. The product was then subjected to storage one month at room temperature (25° C.) for three months (with inspection at monthly intervals) and accelerated aging conditions (40° C.) for six months (with inspection at one, two, three and six month intervals). Results are set out below in TABLE 12.

Oxidation, a prime cause of product instability resulting from adding oxygen or removing hydrogen, can be evinced by discoloration of the active ingredient or matrix layer in which it resides, e.g., as visible to the unassisted eye, or as determinable by conventional colorometric techniques known to the person of skill in the art.

TABLE 12

Stability Data for Batch Composition with Duro-Tak™ 87-900A

| | Initial | RT 25 C./60 F. | | | Accelerated Stability | | | |
|---|---|---|---|---|---|---|---|---|
| Time | | 1 Month | 3 Month | 6 Month | 1 Month | 2 Month | 3 Month | 6 Month |
| Assay (%) | 103.2 | | 97.7 | 103.1 | 100.0 | 100.9 | 96.9 | 101.3 |

RELATED SUBSTANCES (% w/w)

| | | RT 25 C./60 F. | | Accelerated | | | |
|---|---|---|---|---|---|---|---|
| Impurity | Initial | 6 M | | 1 Month | 2 Month | 3 Month | 6 Month |
| Imp. A | 0.031 | 0.130 | | 0.048 | 0.083 | 0.078 | 0.098 |
| Imp. B | 0.0 | 0.014 | | 0.0 | 0.0 | 0.0 | 0.016 |

TABLE 12-continued

| | | | | | | |
|---|---|---|---|---|---|---|
| Highest unknown | 0.033 | 0.327 | 0.239 | 0.260 | 0.228 | 0.334 |
| Total Unknown | 0.090 | 0.644 | 0.333 | 0.401 | 0.352 | 0.624 |
| Total | 0.121 | 0.788 | 0.381 | 0.484 | 0.430 | 0.736 |

Example 13 (Determining Flux Rate Profiles of Examples 1-4)

In vitro pramipexole flux rates from transdermal patches made according to Examples 1 and 2 (Using Duro-Tak™ 87-2287 A) and Examples 3 and 4 (Using Duro-Tak™ 87-900A) was determined and plotted as flux profiles (flux rate over time) in FIGS. 1 and 2.

A flux profile was determined according to conventional methods known to those skilled in the art, using human cadaver skin (4×6) under the following conditions: phosphate buffer of 7.4 pH, temperature 32° C., 300 RPM paddle speed during dissolution, with complete decantations.

A pramipexole transdermal delivery system having a drug releasing interface surface area of 1 cm$^2$ may be used. In the test, the pramipexole transdermal delivery system can be held adhesively on a stainless steel holder, having the drug releasing surface of the patch facing up and immersable in release medium, and positioned at the center of a USP Dissolution Apparatus II with 1 L vessels. Accurately, 600 mL of degassed 0.005N sodium phosphate, pH 7.4 phosphate buffer solution is placed in the vessels and maintained at 32° C. and 300 rpm paddle speed during the dissolution experiment.

At the preset time intervals of 1, 3, 6, 9, 12, 24, 48, 72, 96, 120, 144, and 168 hours, 1 mL portions of the dissolution medium can be withdrawn from the vessels and dispensed into HPLC vials.

Release rates of pramipexole over time from the sample transdermal delivery systems were plotted and the resulting profiles are presented in FIG. 1 and FIG. 2 below.

FIG. 1 shows a flux (or flux rate) ranging from about 1 µg/cm$^2$/hr to about 5 µg/cm$^2$/hr between 24 and 168 hours after treatment is initiated.

FIG. 2 shows a flux (or flux rate) ranging from about 1 µg/cm$^2$/hr to about 6 µg/cm$^2$/hr between 24 and 168 hours.

Example 14 (Determining Flux Rate Profiles of Examples 5-8)

In vitro pramipexole flux rates from transdermal patches made according to Example 5 (using silicone Bio PSA 7-4301), Example 6 (using polyisobutene Duro-Tak™ PIB 612 A, and Examples 7 and 8 (using Duro-Tak™ 87-2287 A) were determined according to the procedures provided in EXAMPLE 13 and plotted as flux profiles in FIG. 3 and cumulatively in FIG. 4.

FIG. 3 shows flux (or flux rates) ranging from about 1 µg/cm$^2$/hr to about 13 µg/cm$^2$/hr between 24 and 168 hours. FIG. 4 shows cumulative release of active ingredient ranging from about 600 to about 900 µg/cm$^2$ over 168 hours for embodiments of the present disclosure, and less than about 200 µg/cm$^2$ over 168 hours for a comparative embodiment of EXAMPLE 6.

Average readings (taken by averaging three readings) used in preparing the flux profiles of FIG. 3 and FIG. 4 are set out below in TABLE 13.

TABLE 13

FLUX DATA For FIG. 3 and FIG. 4

| Label Claim/6.99 cm2 | 5.00 mg | 4.10 mg | 3.59 mg | 3.17 mg |
|---|---|---|---|---|
| | Amount Permeated | | | |
| B. NO. CELL NO. HRS. | Ex. 5 VIB-0716-087 microg/sq · cm Avg | Ex. 6 VIB-0716-089 microg/sq · cm Avg | Ex. 7 VIB-0716-092 microg/sq · cm Avg | Ex. 8 VIB-0716-095 microg/sq · cm Avg |
| 0 | 0 | 0 | 0 | 0 |
| 3 | 13.5 | 6.7 | 30.6 | 21.1 |
| 6 | 45.8 | 17.1 | 78.9 | 65.5 |
| 9 | 83.3 | 27.1 | 126.4 | 109 |
| 12 | 139.3 | 39.5 | 190.5 | 165.9 |
| 24 | 283.7 | 68 | 333 | 295.8 |
| 48 | 471.2 | 101.4 | 503.8 | 450.5 |
| 72 | 658.8 | 119.6 | 615.8 | 544.5 |
| 96 | 787.4 | 133.3 | 678.7 | 598.4 |
| 120 | 869.2 | 145 | 717.7 | 634.3 |
| 144 | 916.8 | 154.1 | 740.8 | 657.6 |
| 168 | 957.3 | 164.1 | 760.8 | 677.3 |
| | Ex. 5 | Ex. 6 | Ex. 7 | Ex. 8 |
| B. NO. CELL NO. HRS. | VIB-0716-087 Flux µg/cm2/hr Avg | VIB-0716-089 Flux µg/cm2/hr Avg | VIB-0716-092 Flux µg/cm2/hr Avg | VIB-0716-095 Flux µg/cm2/hr Avg |
| 0 | 0 | 0 | 0 | 0 |
| 3 | 4.5 | 2.2 | 10.2 | 7 |
| 6 | 10.8 | 3.4 | 16.1 | 14.8 |

TABLE 13-continued

FLUX DATA For FIG. 3 and FIG. 4

| Label Claim/6.99 cm2 | 5.00 mg | 4.10 mg | 3.59 mg | 3.17 mg |
|---|---|---|---|---|
| 9 | 12.5 | 3.3 | 15.8 | 14.5 |
| 12 | 18.6 | 4.1 | 21.4 | 19 |
| 24 | 12 | 2.4 | 11.9 | 10.8 |
| 48 | 7.8 | 1.4 | 7.1 | 6.4 |
| 72 | 7.8 | 0.8 | 4.7 | 3.9 |
| 96 | 5.4 | 0.6 | 2.6 | 2.3 |
| 120 | 3.4 | 0.5 | 1.6 | 1.5 |
| 144 | 2 | 0.4 | 1 | 1 |
| 168 | 1.7 | 0.4 | 0.8 | 0.8 |

Examples 15-18 (Batch Compositions Made with Duro-Tak™ 87-900 A and Varying Levels of Polyvinylpyrrolicone)

Ethanol was added to a glass beaker to which polyvinylpyrrolidone (povidone) Plasdone™ K-90, available from Ashland, Inc. was added and dissolved. Pramipexole free base was then added to the beaker and dissolved to form a pramipexole mixture. The Duro-Tak™ component was then weighed in a glass jar to which was then added the pramipexole mixture with mixing for a suitable time using a stirrer and/or jar roller. The jar rolling was carried out as needed to effectively degas the resulting mixture. The resulting degassed matrix layer precursor mixture was then coated onto one side of a MEDIRELEASE® 2249 film. The uncoated side was then laminated with MEDIFLEX® 1200 backing layer. Crystal growth observations were made after 5 months of storage. Results are set out below in TABLE 14.

TABLE 14

Drug in single adhesive matrix layer with higher levels of PVP in Duro-Tak ™ 87-900 A system

| Batch No. | Ex. 15 0956-151 | Ex. 16 0956-160 | Ex. 17 0956-163 | Ex. 18 0956-166 |
|---|---|---|---|---|
| Pramipexole base | 5.0 | 5.0 | 5.0 | 5.0 |
| Plasdone 90 | 12.5 | 15.0 | 17.5 | 20.0 |
| DT 900 A | 82.50 | 80.0 | 77.5 | 75.0 |
| Ethanol | q.s | q.s. | q.s | q.s. |
| CRYSTAL GROWTH OBSERVATIONS | | | | |
| 25/60 | Crystal Not Observed 5 Months | Crystal Not Observed 5 Months | Crystal Not Observed 5 Months | Crystal Not Observed 5 Months |
| 40/75 | Crystal Not Observed 5 months | Crystal Not Observed 5 Months | Crystal Not Observed 5 months | Crystal Not Observed 5 Months |

Examples 19-23 (Batch Compositions Made with Drug Dispersion Reservoir Layer of BIO PSA-4201 and Contact Layer of Duro-Tak™ 87-900 A with and without Polyvinylpyrrolicone)

SILICONE (BIO-PSA 4201) was weighed out in a glass jar. Pramipexole free base was then weighed out, added to the jar and dispersed to form a pramipexole dispersion which was mixed for a suitable time using a stirrer and/or jar roller. The jar rolling was carried out for a suitable time as needed to effectively degas the resulting mixture. The resulting degassed matrix layer precursor mixture was then coated onto one side of an intermediate release liner (Scotchpak™ 1022) to provide a silicone-coated film. Duro-Tak™ 87-900A coating prepared with and without added Plasdone™ K-90, polyvinylpyrrolidone available from Ashland, Inc., and coated onto one side of an intermediate release liner (Scotchpak™ 1022) to form a Duro-Tak™ 87-900A coated material. The release liner was then removed from the silicone-coated film and the resulting product was then laminated with the Duro-Tak™ 87-900A coated material. Additional information is set out below in TABLE 15.

TABLE 15

MULTI LAYER SYSTEM WITH DRUG DISPERSION RESERVOIR LAYER of SILICONE (BIO-PSA 4201) and CONTACT LAYER (Duro-Tak ™ 900 A)

| Batch No. | Ex. 19 0956-195 | Ex. 20 1087-001 | Ex. 21 1087-006 | Ex. 22 1087-043 | Ex. 23 1087-096 |
|---|---|---|---|---|---|
| Drug Layer (DL) | | | | | |
| Pramipexole base | 5.0 | 5.0 | 5.0 | 7.0 | 15.0 |
| Silicone Bio-PSA 4201 | 95.0 | 95.0 | 95.0 | 93.0 | 85.0 |
| Skin Contact layer (SC) | | | | | |
| Durotak 900 A | Contact Layer 100.0 | Contact Layer 90.0 | Contact Layer 100.0 | Contact Layer 90.0 | Contact Layer 90.0 |

TABLE 15-continued

MULTI LAYER SYSTEM WITH DRUG DISPERSION RESERVOIR LAYER of SILICONE
(BIO-PSA 4201) and CONTACT LAYER (Duro-Tak ™ 900 A)

| Batch No. | Ex. 19<br>0956-195 | Ex. 20<br>1087-001 | Ex. 21<br>1087-006 | Ex. 22<br>1087-043 | Ex. 23<br>1087-096 |
|---|---|---|---|---|---|
| Povidone K 90 | — | 10.0 | — | 10.0 | 10.0 |
| Ethanol | — | q.s | — | q.s | q.s |
| GSM (g/m$^2$) | 100 + 40 | 100 + 40 | 100 + 40 | 100 + 40 | 100 + 40 |

Example 24 (Determining Flux Rate Profiles of Examples 16, 19, and 22)

Figure 5:
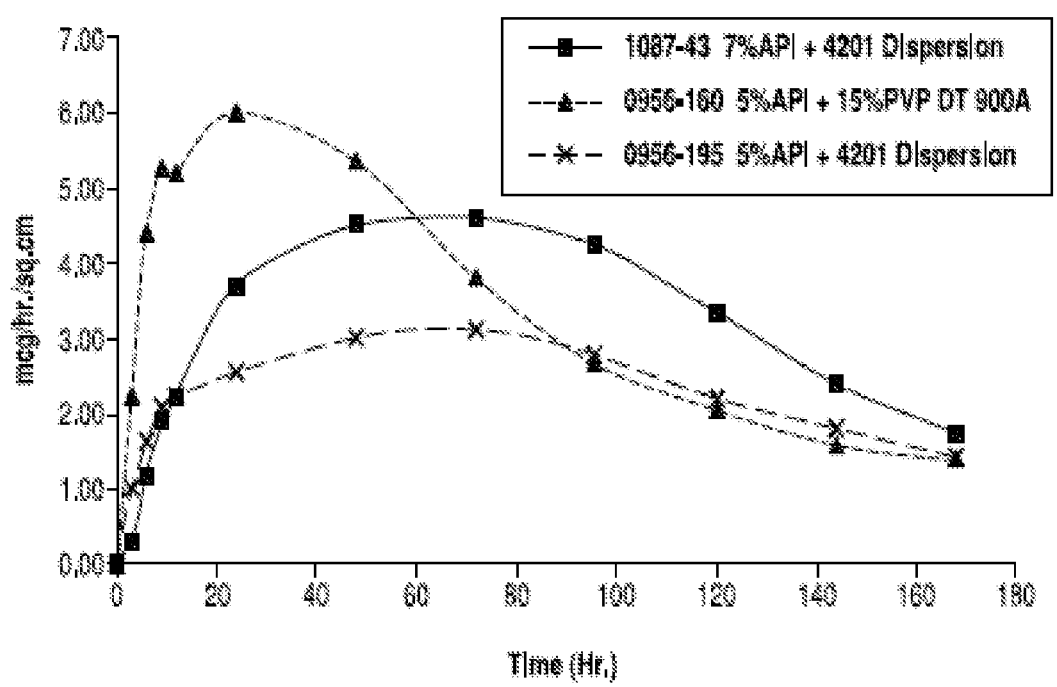
FIG. 5 depicts a flux profile which depicts flux (μg/cm²/hr) plotted over time (168 hrs) for transdermal therapeutic devices of EXAMPLES 16, 19 and 22.
Figure 6:
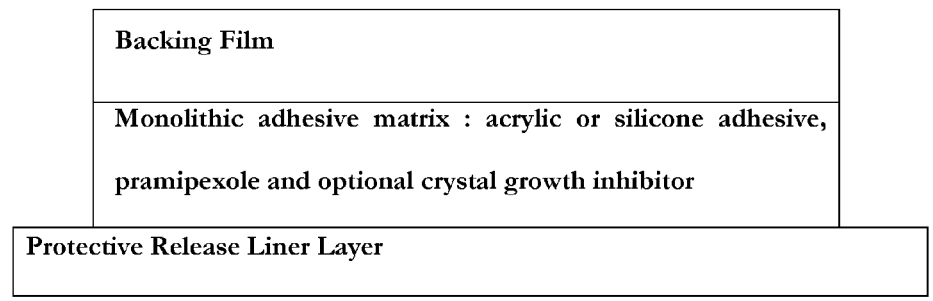
FIG. 6 depicts a schematic elevation drawing of a transdermal patch of the present disclosure.

In vitro pramipexole flux rates from transdermal patches made according to EXAMPLES 16, 19 and 22 were determined according to the procedures provided in EXAMPLE 13 and plotted as flux profiles in FIG. 5.

Examples 25-28 (Batch Compositions Made with Acrylic Drug Dispersion Reservoir Layer of Duro-Tak™ 87-900 A or DuroTak™ 87-2287 with Polyvinylpyrrolicone)

Ethanol was added to a glass beaker to which polyvinylpyrrolidone Plasdone™ K-90 (povidone; PVP K90), available from Ashland, Inc., was added and dissolved. Pramipexole free base was then added to the beaker and dissolved to form a pramipexole mixture. The Duro-Tak™ component was then weighed in a glass jar to which was then added the pramipexole mixture with mixing for a suitable time using a stirrer and/or jar roller. The jar rolling was carried out as needed to effectively degas the resulting mixture. The resulting degassed matrix layer precursor mixture was then coated onto one side of a MEDIRELEASE® 2249 film at a coating weight of either 70 g/m$^2$ or 100 g/m$^2$. The uncoated side was then laminated with MEDIFLEX® 1200 backing layer, as shown in TABLE 16.

TABLE 16

Drug in single adhesive matrix layer with higher levels
of PVP in Duro-Tak ™ 87-900 A system

| Batch No. | Ex. 25<br>0956-001 | Ex. 26<br>0956-016 | Ex. 27<br>0956-031 | Ex. 28<br>0716-194 |
|---|---|---|---|---|
| Pramipexole base | 5.5 | 5.5 | 6 | 6 |
| PVP K90 | 5 | 5 | 10 | 10 |
| DT 2287 | 89.5 | — | — | 84 |
| DT 900 A | — | 89.5 | 84 | — |
| Ethanol | q.s. | q.s. | q.s. | q.s |

Formulations 0716-194 and 0956-031 were coated onto a backing, and formulated into transdermal dosage forms having an area of 7 cm$^2$, containing 2.94 mg pramipexole base per dosage form (2.94 mg/7 cm$^2$). Formulations 0956-001 and 0956-016 were coated onto a backing, and formulated into transdermal dosage forms having an area of 7 cm$^2$, containing 3.85 mg pramipexole base per dosage form (2.94 mg/7 cm$^2$).

Example 29 (Comparative Multi-Layer Adhesive Matrix with Polyvinylpyrrolidone)

A comparative example of the transdermal therapeutic system of the present disclosure was prepared as follows, based on the batch composition used in preparing the active ingredient-containing matrix layers including a reservoir layer and a skin contact layer, made with Duro-Tak™ 87-2287 A as set out in TABLE 17 below. The reservoir layer and the skin contact layer each contain less than 5% w/w of the active ingredient.

TABLE 17

Ex. 29 - Drug Composition Using Multi-Layer
Adhesive Matrix (Batch No. 1087-031)

| Ingredient | % w/w |
|---|---|
| Reservoir Layer | |
| Pramipexole base | 4 |
| PVP K90 | 12.5 |
| Duro-Tak ™ 87-900 A | 83.5 |
| Ethanol | q.s. |
| Contact layer | |
| Pramipexole base | 2 |
| PVP K90 | 12.5 |
| Duro-Tak ™ 87-900 A | 85.5 |
| Ethanol | q.s. |

Ethanol was weighed and added to a glass beaker. Pramipexole free base was then added to the beaker and dissolved to form a pramipexole mixture. The Duro-Tak™ component was then weighed in a glass jar to which was then added the pramipexole mixture with mixing for a suitable time using a stirrer and/or jar roller. The jar rolling was carried out for a suitable time as needed to effectively degas the resulting mixture. The resulting degassed matrix layer precursor mixture was then coated onto one side of a MEDIRELEASE® 2249 film at a coating weight of 90 g/m$^2$. The uncoated side was then laminated with MEDIFLEX® 1200 backing layer.

The formulation for the contact layer was prepared in the same manner as the reservoir layer formulation, and coated onto one side of a MEDIRELEASE® 2249 film at a coating weight of 40 g/m$^2$. The release liner was then removed from the pramipexole-containing laminate and laminated with the contact layer, providing a multi-layer adhesive matrix having a skin contact layer.

Example 30 (Determining Flux Rate Profiles of Examples 16, 19, 22, and 29)

Figure 7:
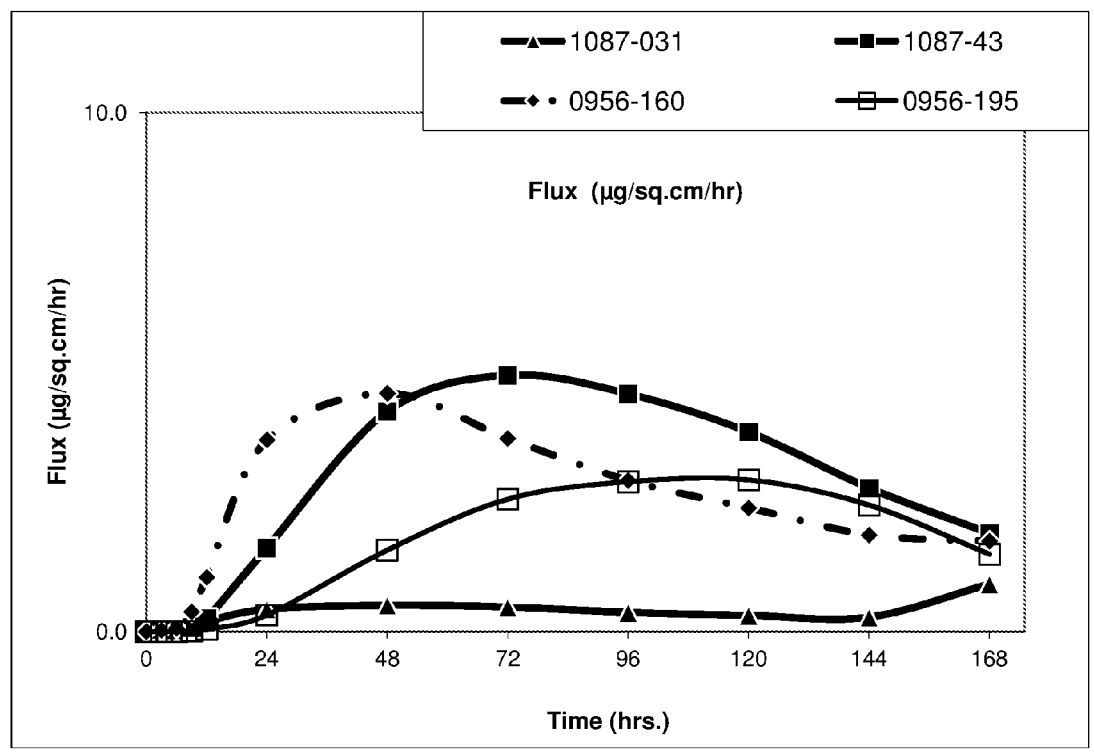
FIG. 7 depicts a flux profile which depicts flux (μg/cm²/hr) plotted over time (168 hrs) for transdermal therapeutic devices of EXAMPLES 16, 19, 22, and 29.
Figure 8:
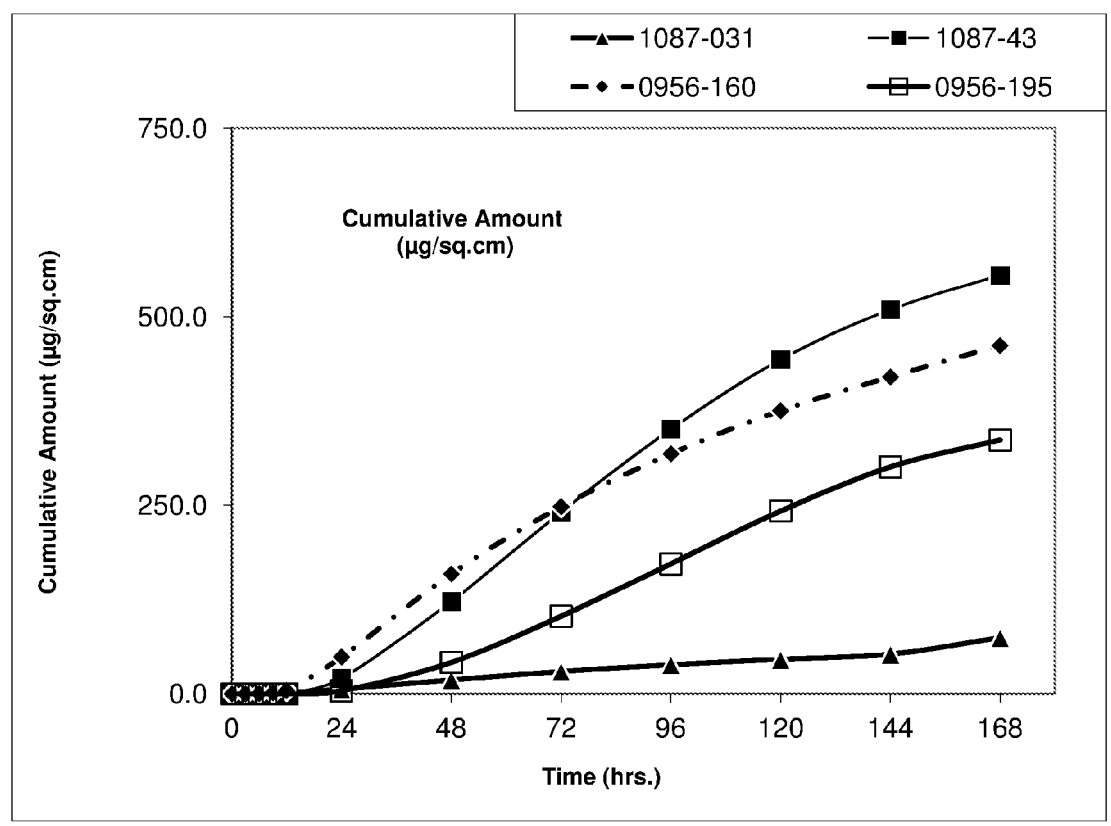
FIG. 8 depicts cumulative flux profile which depicts flux (μg/cm²) plotted over time (168 hrs) for transdermal therapeutic devices of EXAMPLES 16, 19, 22, and 29.

In vitro pramipexole flux rates from transdermal patches made according to Examples 19 and 22 (using a silicone reservoir layer and a Duro-Tak contact layer), Example 16 (using a Duro-Tak monolayer), and comparative Example 29 (using a drug-containing Duro-Tak reservoir layer and a drug-containing Duro-Tak contact layer) were determined according to the procedures provided in EXAMPLE 13 and plotted as flux profiles in FIG. 7 and cumulatively in FIG. 8.

FIG. 7 shows peak flux (or flux rates) ranging from about 2.9 μg/cm$^2$/hr to about 5.2 μg/cm$^2$/hr for working examples 16, 19, and 22; and less than 1 μg/cm$^2$/hr for comparative Example 29. FIG. 8 shows cumulative release of active ingredient ranging from about 335 to about 555 μg/cm$^2$ over 168 hours for working examples 16, 19, and 22, and less than about 75 μg/cm² over 168 hours for comparative Example 29.

Average readings (taken by averaging three readings) used in preparing the flux profiles of FIG. 7 and FIG. 8 are set out below in TABLE 18.

TABLE 18

FLUX DATA For FIG. 7 and FIG. 8
Amount Permeated

| B. NO.<br>HRS. | Ex. 29<br>1087-031<br>microg/sq · cm | Ex. 22<br>1087-043<br>microg/sq · cm | Ex. 16<br>0956-160<br>microg/sq · cm | Ex. 19<br>0956-195<br>microg/sq · cm |
|---|---|---|---|---|
| 0 | 0.0 | 0.0 | 0.0 | 0.0 |
| 3 | 0.1 | 0.1 | 0.1 | 0.0 |
| 6 | 0.2 | 0.2 | 0.3 | 0.0 |
| 9 | 0.5 | 0.5 | 1.4 | 0.0 |
| 12 | 1.0 | 1.2 | 4.5 | 0.2 |
| 24 | 6.2 | 20.5 | 48.8 | 4.0 |
| 48 | 18.4 | 122.3 | 159.0 | 41.6 |
| 72 | 29.8 | 240.9 | 248.2 | 102.9 |
| 96 | 38.5 | 350.9 | 318.1 | 172.2 |
| 120 | 45.9 | 443.2 | 375.4 | 242.4 |
| 144 | 52.4 | 509.5 | 420.1 | 300.9 |
| 168 | 74.5 | 554.9 | 461.9 | 336.6 |

| B. NO.<br>HRS. | Ex. 29<br>1087-031<br>Flux μg/cm2/hr | Ex. 22<br>1087-043<br>Flux μg/cm2/hr | Ex. 16<br>0956-160<br>Flux μg/cm2/hr | Ex. 19<br>0956-195<br>Flux μg/cm2/hr |
|---|---|---|---|---|
| 0 | 0.0 | 0.0 | 0.0 | 0.0 |
| 3 | 0.0 | 0.0 | 0.0 | 0.0 |
| 6 | 0.0 | 0.0 | 0.1 | 0.0 |
| 9 | 0.1 | 0.1 | 0.4 | 0.0 |
| 12 | 0.2 | 0.2 | 1.0 | 0.0 |
| 24 | 0.4 | 1.6 | 3.7 | 0.3 |
| 48 | 0.5 | 4.2 | 4.6 | 1.6 |
| 72 | 0.5 | 4.9 | 3.7 | 2.6 |
| 96 | 0.4 | 4.6 | 2.9 | 2.9 |
| 120 | 0.3 | 3.8 | 2.4 | 2.9 |
| 144 | 0.3 | 2.8 | 1.9 | 2.4 |
| 168 | 0.9 | 1.9 | 1.7 | 1.5 |

Example 31 (Determining Flux Rate Profiles of Examples 25, 26, 27, and 28)

Figure 9:
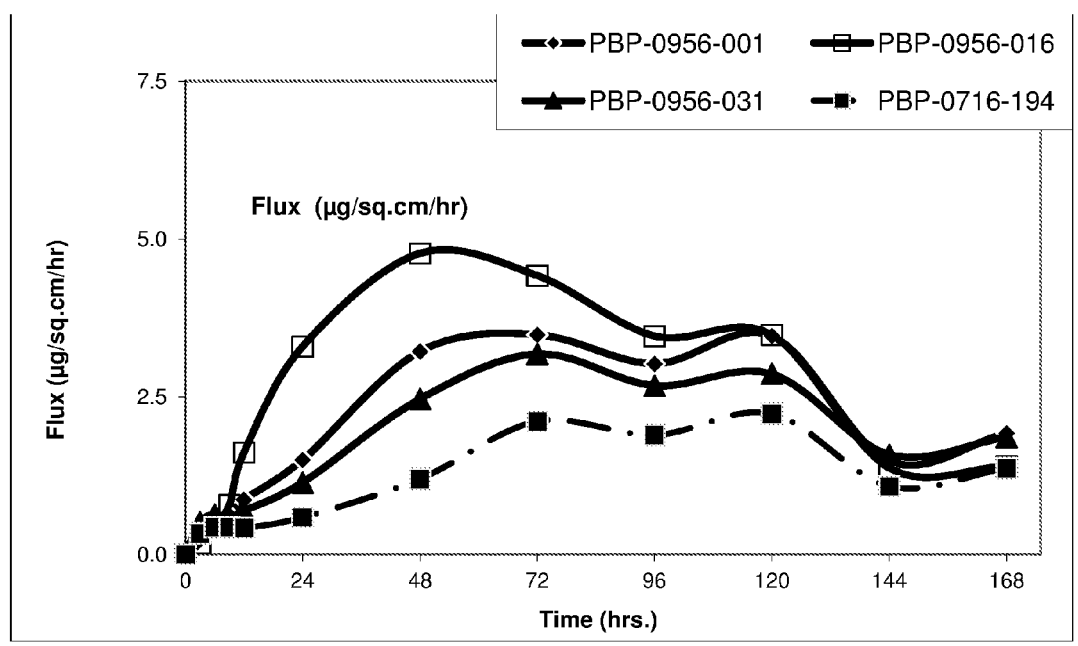
FIG. 9 depicts a flux profile which depicts flux (μg/cm²/hr) plotted over time (168 hrs) for transdermal therapeutic devices of EXAMPLES 25 to 28.
Figure 10:
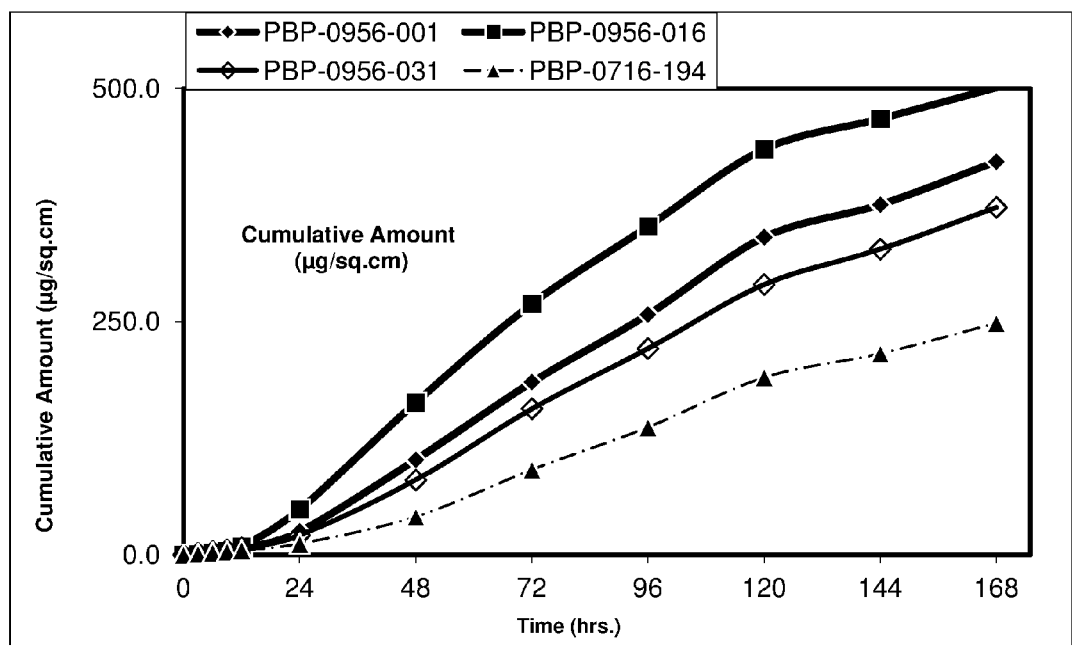
FIG. 10 depicts cumulative flux profile which depicts flux (μg/cm²) plotted over time (168 hrs) for transdermal therapeutic devices of EXAMPLES 25 to 28.

In vitro pramipexole flux rates from transdermal patches made according to Examples 25, 26, 27, and 28 (using a Duro-Tak monolayer) were determined according to the procedures provided in EXAMPLE 13 and plotted as flux profiles in FIG. 9 and cumulatively in FIG. 10.

FIG. 9 shows peak flux (or flux rates) ranging from about 2.2 μg/cm²/hr to about 4.4 μg/cm²/hr for examples 25, 26, 27, and 28. FIG. 10 shows cumulative release of active ingredient ranging from about 250 to about 480 μg/cm² over 168 hours for examples 25, 26, 27, and 28.

Average readings (taken by averaging three readings) used in preparing the flux profiles of FIG. 9 and FIG. 10 are set out below in TABLE 19.

TABLE 19

FLUX DATA For FIG. 9 and FIG. 10

| Label Claim/6.99 cm2 | 5.00 mg | 4.10 mg | 3.59 mg | 3.17 mg |
|---|---|---|---|---|

Amount Permeated

| B. NO.<br>HRS. | Ex. 25<br>0956-001<br>microg/sq · cm | Ex. 26<br>0956-016<br>microg/sq · cm | Ex. 27<br>0956-031<br>microg/sq · cm | Ex. 28<br>0716-194<br>microg/sq · cm |
|---|---|---|---|---|
| 0 | 0.0 | 0.0 | 0.0 | 0.0 |
| 3 | 1.3 | 0.6 | 1.3 | 0.9 |
| 6 | 3.3 | 1.8 | 3.0 | 2.2 |
| 9 | 5.3 | 3.8 | 4.8 | 3.4 |
| 12 | 8.0 | 7.7 | 7.0 | 5.0 |
| 24 | 26.0 | 41.2 | 23.4 | 11.8 |
| 48 | 104.3 | 147.2 | 91.3 | 41.2 |

TABLE 19-continued

FLUX DATA For FIG. 9 and FIG. 10

| Label Claim/6.99 cm2 | 5.00 mg | 4.10 mg | 3.59 mg | 3.17 mg |
|---|---|---|---|---|
| 72 | 189.9 | 247.5 | 170.5 | 93.4 |
| 96 | 263.6 | 328.3 | 236.2 | 139.2 |
| 120 | 345.2 | 411.1 | 303.7 | 191.4 |
| 144 | 380.6 | 446.3 | 339.5 | 216.7 |
| 168 | 426.6 | 481.8 | 381.0 | 250.1 |

| B. NO.<br>HRS. | Ex. 25<br>0956-001<br>Flux μg/cm2/hr | Ex. 26<br>0956-016<br>Flux μg/cm2/hr | Ex. 27<br>0956-031<br>Flux μg/cm2/hr | Ex. 28<br>0716-194<br>Flux μg/cm2/hr |
|---|---|---|---|---|
| 0 | 0.0 | 0.0 | 0.0 | 0.0 |
| 3 | 0.4 | 0.2 | 0.4 | 0.3 |
| 6 | 0.7 | 0.4 | 0.6 | 0.4 |
| 9 | 0.7 | 0.7 | 0.6 | 0.4 |
| 12 | 0.9 | 1.5 | 0.7 | 0.5 |
| 24 | 1.5 | 2.8 | 1.4 | 0.6 |
| 48 | 3.3 | 4.4 | 2.8 | 1.2 |
| 72 | 3.6 | 4.2 | 3.3 | 2.2 |
| 96 | 3.1 | 3.4 | 2.7 | 1.9 |
| 120 | 3.4 | 3.5 | 2.8 | 2.2 |
| 144 | 1.5 | 1.5 | 1.5 | 1.1 |
| 168 | 1.9 | 1.5 | 1.7 | 1.4 |

Although various exemplary embodiments have been described in detail with particular reference to certain exemplary aspects thereof, it should be understood that the subject matter disclosed herein is capable of other different embodiments, and its details are capable of modifications in various obvious respects. As is readily apparent to those skilled in the art, variations and modifications can be affected while remaining within the spirit and scope of the disclosure. Accordingly, the foregoing disclosure, description, and figures are for illustrative purposes only, and do not in any way limit the invention, which is defined only by the claims.

What is claimed is:

1. A transdermal therapeutic system (TTS) for the administration of one or more active ingredients selected from the group consisting of pramipexole, pharmaceutically acceptable pramipexole salts, and pharmaceutically acceptable pramipexole derivatives, the system comprising:
   (i) a substantially active-ingredient-impermeable backing layer,
   (ii) at least one matrix layer which contains at least about 5% to 10% w/w active ingredient(s), and
   (iii) a substantially impermeable protective release liner layer which releasably contacts the matrix layer or other adhesive layer;
wherein 1) the matrix layer comprises an adhesive selected from acrylate-based adhesive and silicone-based adhesive, 2) the transdermal therapeutic system provides a therapeutically effective administration of the active ingredient(s), at a flux rate ranging from 1 μg/cm$^2$/hr to 4.6 μg/cm$^2$/hr between the 96$^{th}$ and 168$^{th}$ hour after treatment is initiated, and 3) the matrix layer is color-stable and lacks crystal growth of the active ingredient, over an extended storage period of at least one of 30 or more days, 90 or more days, and 180 or more days.

2. The transdermal therapeutic system of claim 1, wherein the active-ingredient-containing matrix layer contains from about 5.5% to about 7% w/w active ingredient(s) and provides a therapeutically effective flux profile ranging from about 1 μg/cm$^2$/hr to 4.6 μg/cm$^2$/hr between the 96$^{th}$ hour and 168$^{th}$ hour after treatment is initiated.

3. The transdermal therapeutic system of claim 1, wherein the active-ingredient-containing matrix layer provides a therapeutically effective flux profile ranging from about 1.2 μg/cm$^2$/hr to 4.6 μg/cm$^2$/hr 168 hours after treatment is initiated.

4. The transdermal therapeutic system of claim 1, wherein the active ingredient comprises pramipexole free base.

5. The transdermal therapeutic system of claim 1, wherein the active ingredient comprises one or more salts of pramipexole comprising reaction products of pramipexole or a pramipexole derivative and an acid.

6. The transdermal therapeutic system of claim 1, wherein the matrix layer is self-adhesive.

7. The transdermal therapeutic system of claim 1, wherein the matrix layer comprises an acrylate-based adhesive comprising polyacrylate lacking a carboxylic acid functional group.

8. The transdermal therapeutic system of claim 7, wherein the matrix layer comprises a polymer material free of solubilizers and/or crystal growth inhibitors.

9. The transdermal therapeutic system of claim 7, wherein the matrix layer comprises 0 wt. % to about 20 wt. % of a solubilizer and/or crystal growth inhibitor.

10. The transdermal therapeutic system of claim 7, wherein the matrix layer comprises from about 2.5 wt. % to about 17.5 wt. % of a solubilizer and/or crystal growth inhibitor.

11. The transdermal therapeutic system of claim 7, wherein the matrix layer comprises about 10 wt. % of a solubilizer and/or crystal growth inhibitor.

12. The transdermal therapeutic system of claim 9, wherein the solubilizer and/or crystal growth inhibitor is selected from the group consisting of optionally saturated and/or unsaturated fatty alcohols each containing from 8 to 18 carbon atoms; tea tree oil; saturated and/or unsaturated cyclic ketones; alkyl methyl sulfoxides; saturated and/or unsaturated fatty acids each containing from 8 to 18 carbon atoms; esters and salts thereof; natural vitamin E; synthetic vitamin E and/or vitamin E derivatives; sorbitan fatty acid esters and/or ethoxylated sorbitan fatty acid esters; azones (laurocapram); 1-alkylpyrrolidone; polyvinylpyrrolidone;

block copolymers of polyethylene glycol and dimethylsiloxane with a cationic group at one end; polysiloxanes; polyoxyethylene-10-stearyl ether; mixture of polyoxyethylene-10-stearyl ether and glyceryl dilaurate; dodecyl-2-(N,N-dimethylamino)-propanol tetradecanoate and/or dodecyl-2-(N,N-dimethylamino)-propionate; N-acetylprolinate esters with >8 carbon atoms; non-ionic surfactants, for example lauryl ethers and/or esters of polyoxyethylene; dimethyl(arylimino)sulfuran; mixture of oleic acid analogues and propylene glycol; mixture of octyl salicylate, isopropyl myristate, isopropyl palmitate, octylmethoxy cinnamate and laurocapram or a mixture of individual components; phospholipids; highly dispersed silicon dioxide; polyoxyethylene-7-glycerol monococoate; 2-octyldodecanol or a mixture of various individual components.

13. The transdermal therapeutic system of claim 9, wherein the solubilizer and/or crystal growth inhibitor is polyvinylpyrrolidone.

14. The transdermal therapeutic system of claim 1, wherein the active ingredient matrix layer contains from about 5.5% to about 7% w/w active ingredient(s).

15. A method for preparing a transdermal therapeutic system according to claim 1 which comprises:
   i) providing an active-ingredient containing matrix layer by:
      1) forming a mixture comprising a) active ingredient pramipexole free base, b) a solvent selected from methanol, ethanol, n-propanol, iso-propanol, n-butanol, iso-butanol and tert-butanol, acetone, pentane, hexane, heptane, ethyl acetate, isopropanol, toluene, xylene, 2,4-pentanedione, and water, and c) an optional solubilizer and/or crystal growth inhibitor;
      2) dissolving the mixture to provide a dissolved mixture;
      3) combining the dissolved mixture with a matrix forming ingredient to form a pramipexole-containing matrix precursor mixture; and
      4) optionally degassing the matrix precursor mixture to provide a degassed matrix precursor mixture;
   ii) coating one side of a release liner film with the matrix precursor mixture or optionally degassed matrix precursor mixture; and
   iii) laminating a backing film to the coated side of the release liner film.

16. The method of claim 15, wherein the solvent comprises ethanol, the dissolving step comprises sonication, the optional solubilizer and/or crystal growth inhibitor comprises polyvinylpyrrolidone, and the matrix forming ingredient comprises an adhesive selected from acrylate-based adhesive and silicone-based adhesive.

17. The method of claim 16, wherein the adhesive comprises polyacrylate lacking a carboxylic acid functional group.

18. The method of claim 15, wherein the optional solubilizer and/or crystal growth inhibitor comprises polyvinylpyrrolidone.

19. The method of claim 15, wherein the adhesive comprises silicone-based adhesive, silicone oil, and colloidal silicon dioxide.

20. A method for administering pramipexole to a human subject in need thereof, which method comprises:
   i) providing a transdermal dosage form according to claim 1; and
   ii) applying the dosage form onto an area of skin of the subject in an amount sufficient to provide a therapeutic concentration of pramipexole in the bloodstream or the subject.

21. The method according to claim 20, wherein the human subject is in need of pramipexole to treat a neurological disorder.

22. The method according to claim 21, wherein the human subject is in need of pramipexole to treat a condition selected from the group consisting of Parkinson's Disease, Restless Legs Syndrome, Tourette's Syndrome, Chronic Tic Disorder, Essential Tremor, and Attention Deficit Hyperactivity Disorder.

23. The method according to claim 20, which comprises applying up to about 10 grams of the dosage form daily to a skin surface area of about 50 to about 500 cm$^2$.

24. The method according to claim 20, wherein the method comprises applying the dosage form in a weekly single dose.

25. A method for preparing a transdermal therapeutic system according to claim 1 which comprises:
   i) providing an active-ingredient containing matrix layer by:
      1) forming a mixture comprising a) active ingredient pramipexole free base, b) a solvent and/or dispersant selected from methanol, ethanol, n-propanol, iso-propanol, n-butanol, iso-butanol and tert-butanol, acetone, pentane, hexane, heptane, ethyl acetate, isopropanol, toluene, xylene, 2,4-pentanedione, and water, and c) an optional solubilizer and/or crystal growth inhibitor;
      2) dissolving and/or dispersing the mixture to provide a dissolved and/or dispersed mixture;
      3) combining the dissolved and/or dispersed mixture with a matrix forming ingredient to form a pramipexole-containing matrix precursor mixture; and
      4) optionally degassing the matrix precursor mixture to provide a degassed matrix precursor mixture;
   ii) coating one side of a release liner film with the matrix precursor mixture or optionally degassed matrix precursor mixture; and
   iii) laminating a backing film to the coated side of the release liner film.

* * * * *